US007449335B2

(12) United States Patent
Weeks et al.

(10) Patent No.: US 7,449,335 B2
(45) Date of Patent: Nov. 11, 2008

(54) PRECISE CUTTING

(75) Inventors: J. Troy Weeks, Boise, ID (US); Caius Rommens, Boise, ID (US); Jingsong Ye, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 0 days.

(21) Appl. No.: 11/493,042

(22) Filed: Jul. 26, 2006

(65) Prior Publication Data

US 2007/0033678 A1    Feb. 8, 2007

Related U.S. Application Data

(60) Provisional application No. 60/702,638, filed on Jul. 27, 2005.

(51) Int. Cl.
*C12N 15/84*    (2006.01)
*C12N 15/82*    (2006.01)
(52) U.S. Cl. .................. 435/469; 435/468; 800/278
(58) Field of Classification Search ................. None
See application file for complete search history.

(56) References Cited

U.S. PATENT DOCUMENTS

| 5,286,635 A * | 2/1994 | Hanson et al. ............ 800/294 |
| 5,948,956 A * | 9/1999 | Lee et al. ................. 800/320 |
| 2003/0221213 A1 | 11/2003 | Rommens et al. |
| 2004/0003434 A1* | 1/2004 | Weeks et al. ............. 800/294 |

FOREIGN PATENT DOCUMENTS

| EP | 0 267 159 | 11/1987 |
| WO | WO 00/56906 A | 9/2000 |
| WO | WO 01/25455 A | 4/2001 |
| WO | WO 02/36786 A | 5/2002 |
| WO | WO 03/079765 A2 | 10/2003 |
| WO | WO 2004/007694 A2 | 1/2004 |

OTHER PUBLICATIONS

Broothaerts et al. 2005, Nature 433:629-633.*
Tisserat, in Plant Cell Culture, ed R.A. Dixon, 1985, IRL Press, Oxford, pp. 79-90, especially p. 80, Table 1, p. 82, and Table 4, pp. 85-90.*
Hansen et. al., 1999, Trends in plant Science, vol. 4, pp. 226-231, see p. 230.*
Hansen et al 1999, Trends in Plant Science 4(6):226-231.*
Atlung, T., et al., "Low-Temperature-Induced DnaA Protein Synthesis Does Not Change Initiation Mass in *Escherichia coli* K-12", Sep. 1999, vol. 181, No. 18, pp. 5557-5562, *Journal of Bacteriology*.
Austin, S., et al., "Production and Field Performance of Transgenic alfalfa (*Medicago sativa* L.) Expressing Alpha-Arnylase and Manganese-Dependent Lignin Peroxidase", 1995, vol. 85, Nos. 1-3, pp. 381-393, *Euphytica*, Netherlands.
Bevan, M., "Binary *Agrobacterium* Vectors for Plant Transformation", 1984, vol. 12, No. 22, pp. 8711-8721, *Nucleic Acids Research—IRL Press Limited*, Oxford, England.

Bingham, E.T., "Registration of Alfalfa Hybrid Regen-Sy Germplasm for Tissue Culture and Transformation Research", Jul.-Aug. 1991, vol. 31, No. 4, pp. 1098, *Crop Science—A Journal Serving the International Community of Crop Scientists*.
Broothaerts, W., "Gene Transfer to Plants by Diverse Species of Bacteria", Feb. 10, 2005, vol. 433, pp. 629-633, *Nature*.
Charity, J.A., "*Agrobacterium*-Mediated Transformation of *Pinus radiata* Organogenic Tissue Using Vacuum-Infiltration", 2002, vol. 70, pp. 51-60, *Plant Cell, Tissue and Organ Culture*.
Chilton, M., "A Vector for Introducing New Genes into Plants", Jun. 1983, vol. 248, No. 6., pp. 51-59, *Scientific American*.
Cornejo, M-J., "Activity of a Maize Ubiquitin Promoter in Transgenic Rice", 1993, vol. 23, pp. 567-581, *Plant Molecular Biology*, Belgium.
De La Riva, G., "*Agrobacterium tumefaciens*: A Natural Tool for Plant Transformation", Dec. 15, 1998, vol. 1, No. 3, pp. 118-133, *EJB Electronic Journal of Biotechnology*, Chile.
Gould, J. H., "Adaptation of cotton Shoot Apex Culture to *Agrobacterium*-Mediated Transformation", 1998, vol. 16, pp. 1-10, *Plant Molecular Biology Reporter*, Netherlands.
Guo, D., et al., "Downregulation Of Caffeic Acid 3-*O*-Methyltransferase and Calfeoyl CoA 3-*O*-Methyltransferase in Transgenic Alfalfa: Impacts on Lignin Structure and Implications for the Biosynthesis of G and S Lignin", Jan. 2001, vol. 13, pp. 73-88, *The Plant Cell*.
Guo, D., et al., "Improvement of In-Rumen Digestibility of Alfalfa Forage by Genetic Manipulation of Lignin *O*-Methyltransferases", 2001, vol. 10., pp. 457-464, *Transgenic Research*, Netherlands.
Jefferson, R. A., "GUS Fusions: β-Glucuronidase as a Sensitive and Versatile Gene Fusion Marker in Higher Plants", 1987, vol. 6, No. 13, pp. 3901-3907, *The EMBO Journal—IRL Press Limited*, Oxford, England.
Khoudi, H., et al., "An Alfalfa Rubisco Small Subunit Homologue Shares *cis*-Acting Elements with the Regulatory Sequences of the RbcS-3A Gene from Pea", 1997, vol. 197, pp. 343-351, *Gene*.
Koncz, C., et al., "The Promoter of TL-DNA Gene 5 Controls the Tissue-Specific Expression of Chimaeric Genes Carried by a Novel Type of *Agrobacterium* Binary Vector", 1986, vol. 204, pp. 383-396, *Mol. Gen. Genet*.
Liang, X., et al., "Developmental and Environmental Regulation of a Phenylalanine Ammonia-Lyase-β-Glucuronidase Gene Fusion in transgenic Tobacco Plants", Dec. 1989, vol. 86, pp. 9284-9288, *Proc. Natl, Acad. Sci*, USA.
Lin, J., et al., "Effects of *Agrobacterium* Cell Concentration on the Transformation Efficiency of Tobacco and *Arabidopsis thaliana*", 1994, vol. 16, No. 3, pp. 72-77, *Focus*.
Maniatis, T., et al., "An Extensive Network of Coupling Among Gene Expression Machines", Apr. 4, 2002, vol. 416, pp. 499-506, *Nature*.
Murashige, T., et al., "A Revised Medium for Rapid Growth and Bio Assays with Tobacco Tissue Cultures", 1962, vol. 15, pp. 473-497, *Physiologia Plantarum*.

(Continued)

*Primary Examiner*—Stuart F. Baum
*Assistant Examiner*—Li Zheng
(74) *Attorney, Agent, or Firm*—Foley & Lardner LLP

(57) ABSTRACT

The present invention provides methods for enhancing plant transformation. One such method entails making an excision in a selected seedling at the point where two cotyledons meet, and then vortexing the cut seedling in a solution comprising a transforming bacterium such as *Agrobacterium*.

7 Claims, 1 Drawing Sheet

OTHER PUBLICATIONS

Rogers, J. C., "Two Barley α-Amylase Gene Families Are Regulated Differently in Aleurone Cells", Mar. 25, 1985, vol. 260, No. 6, pp. 3731-3738, *The Journal of Biological Chemistry* USA.

Rohini, V. K., "Embryo Transformation, A Practical Approach for Realizing Transgenic Plants of Safflower (*Carthamus tinctorius* L.)", 2000, vol. 86, pp. 1043-1049, *Annals of Botany*.

Trick, H. N., et al., "SAAT: Sonication-Assisted *Agrobacterium*-Mediated Transformation", Jun. 1997, vol. 6, No. 4., pp. 329-336, *Transgenic Research*.

Van Montagu, M., "The Interaction of *Agrobacterium* Ti-Plasmid DNA and Plant Cells [and Discussion]", Nov. 19, 1980, vol. 210, No. 1180, pp. 351-365, *Proc. R. Soc. Lond B, Biol. Sci.—The Royal Society*.

Fisscher, et al., "Identification of Potential Regulatory Elements In The Far-Upstream Region Of The *Arabidopsis thaliana* Plastocyanin Promoter," 1994, vol. 26, pp. 873-886, *Plant Molecular Biology*.

Pwee, et al., "The Pea Plastocyanin Promoter Directs Cell-Specific But Not Full Light-Regulated Expression In Transgenic Tobacco Plants,"1993, vol. 3 No. 3, pp. 437-449, *The Plant Journal*.

Rommens, C.M., "Crop Improvement through Modification of the Plant's Owned Genome," May 2004, vol. 135, pp. 421-431, *Plant Physiology*.

* cited by examiner

SEQUENCE LISTING

```
<160> NUMBER OF SEQ ID NOS: 7

<210> SEQ ID NO 1
<211> LENGTH: 493
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 1
ccggcgaccc gccgcatcca taccgccagt tgtttaccct cacaacgttc cagtaaccgg        60
gcatgttcat catcagtaac ccgtatcgtg agcatcctct ctcgtttcat cggtatcatt       120
acccccatga acagaaattc ccccttacac ggaggcatca agtgaccaaa caggaaaaaa       180
ccgcccttaa catggcccgc tttatcagaa gccagacatt aacgcttctg gagaaactca       240
acgagctgga cgcggatgaa caggcagaca tctgtgaatc gcttcacgac cacgctgatg       300
```

```
agctttaccg cagctgcctc gcgcgtttcg gtgatgacgg tgaaaacctc tgacacatgc    360
agctcccgga gacggtcaca gcttgtctgt aagcggatgc cgggagcaga caagcccgtc    420
agggcgcgtc agcgggtgtt ggcgggtgtc ggggcgcagc catgacccag tcacgtagcg    480
atagcggagt gta                                                        493
```

<210> SEQ ID NO 2
<211> LENGTH: 830
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 2

```
gtacacaggg gcagagagag gtgagtcgtc tttctggtag ggctggtgtt ggggatagtg     60
gttggtttga gagtcaggtg gtgaggaggg ttggcgatgg ggttgatacg ttgttttggt    120
tggataggtg gttaggagat gctccttttt gtgtttgttt caggaggttg tttgagttaa    180
cagagaacaa atttgtgtct gtggctaatt tgttatctgt tgactcggag cagtgggggg    240
aggtgttgag gtgaagcgta tggtggcaga ggtggtggca gaggtgaagc gtatggtggc    300
agctgaggga ggcagtgtac acagaggtgg agagagagga gagagaagag agaagagaga    360
gaaaatggag aagagagaag agaagagaga gaagacaaat ttttgtgtgt gtgaccaaac    420
caaaattctt ggtcctggtc cacacaagat tttctcccaa ccaaggtaca gaataccac     480 gatccaagag tgccacgttg caacatcata accgttcaat agtaagagat aatcgaacgg    540
ccataattaa ttttcaacaa acccactttt ttcctcctac ttttgcaact tgtccctcat    600
cacctaccaa acacacatag cacaccaaca cataataa tattataata attgtaaata     660
tatgtagcct ccaaattaga aagaaacctc tatataaagc ctaactactt ccttcacaaa    720
tcaggaaatt cacaactcta atattcattt cttttcctaat cattagaatt ccattctta    780 taaaattcta ggtaccacca cacaacaaat aaaggaacat taatcaatac                830
```

<210> SEQ ID NO 3
<211> LENGTH: 1025
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3

```
ctagaatagt ggaccagtta ggtaggtgga gaaagaaatt attaaaaaaa tatatttata     60
tgttgtcaaa taactcaaaa atcataaaag tttaagttag caagtgtgca cattttatt    120 tggacaaaag tattcaccta ctactgttat aaatcattat taaacattag agtaaagaaa    180
tatggatgat aagaataaga gtagtgatat tttgacaaca attttgttac aacatttgag    240
aaaattttgt tgttctctct tttcattggt caaaaacaat agagagagag agagaaaaag    300
gaagagggag aataaaaaca taatgtgagt atgagagaga aagttgtaca aaagttgtac    360
caaaatggtt gtacaaatat cattgaggaa tttgacaaaa gctacacaaa taagggttaa    420
ttgctgtaaa taaataagga tgacgcatta gagagatgta ccattagaga attttttggca   480 agtcattaaa aagaaagaat aaattatttt taaaattaaa agttgagtca tttgattaaa    540
catgtgatta tttaatgaat tgatgagaga gttggattaa agttgtatta atgattagaa    600
```

| | |
|---|---|
| tttggtgtca aatttaattt gacatttgat cttttcctat atattgcccc atagagtcat | 660 |
| ttaactcatt tttatatttc atagatcaaa taagagaaat aacggtatat taatccctcc | 720 |
| aacaaaaaaa aaaaaaaaac ggtatattta ctaaaaaatc taagccacgt aggaggataa | 780 |
| catccaatcc aaccaatcac aacaatcctg atgagataac ccactttaag cccacgcact | 840 |
| ctgtggcaca tctacattat ctaaatcaca cattcttcca cacatctgag ccacacaaaa | 900 |
| accaatccac atctttatca tccattctat aaaaaatcac actttgtgag tctacacttt | 960 |
| gattcccttc aaacacatac aaagagaaga gactaattaa ttaattaatc atcttgagag | 1020 |
| aaagc | 1025 |

<210> SEQ ID NO 4
<211> LENGTH: 422
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 4

| | |
|---|---|
| catttgagaa tttactatct gccattgaag gaacattttt ttctctccat ttgttctgtt | 60 |
| tgtaatttcc ttttcttttt aaaggaaatg tctccagtgt tttttcggtc tttgctttcg | 120 |
| gattttgaaa tgcaaataga tggataagag ttaattaatg aaatgatact tttattcatt | 180 |
| ctcaaattag tttcattaat ggatatataa agataaagta ataactgcgc ctatgcttcc | 240 |
| tttgcattga agcaactgaa ctttacctaa ttgaaatatc tttacccttg caactaaat | 300 |
| gagtgaatga tgaattggtc gtcgaaattg tgagcatttt tgtcaaaata gtccctgaaa | 360 |
| tatgctattt gagaaataaa tcctgaaact gtaacgcaac agtaagaatg tcactttatt | 420 |
| tc | 422 |

<210> SEQ ID NO 5
<211> LENGTH: 10171
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 5

| | |
|---|---|
| tctagattat gcgggctaac gggctgcccg cggcccttc gggctagccc taacgggtac | 60 |
| cgggccccgg caggatgtat acagaggtat actttggtag ttcgtcagtt cgtcagttcg | 120 |
| tcagttcgtc agttcgtcag ttcgtcaact agttgtgaat aagtcgctgt gtatgtttgt | 180 |
| ttgagatctc taagagaaaa gagcgtttat tagaataacg gatatttaaa agggcgtgaa | 240 |
| aaggtttatc cgttcgtcca tttgtatgtc tcgagcatgc caaccacagg gttcccctcg | 300 |
| ggatcaaagt actttgatcc aacccctccg ctgctatagt gcagtcggct tctgacgttc | 360 |
| agtgcagccg tcttctgaaa acgacatgtc gcacaagtcc taagttacgc gacaggctgc | 420 |
| cgccctgccc ttttcctggc gttttcttgt cgcgtgtttt agtcgcataa agtagaatac | 480 |
| ttgcgactag aaccggagac attacgccat gaacaagagc gccgccgctg gcctgctggg | 540 |
| ctatgcccgc gtcagcaccg acgaccagga cttgaccaac caacgggccg aactgcacgc | 600 |
| ggccggctgc accaagctgt tttccgagaa gatcaccggc accaggcgcg accgcccgga | 660 |
| gctggccagg atgcttgacc acctacgccc tggcgacgtt gtgacagtga ccaggctaga | 720 |
| ccgcctggcc cgcagcaccc gcgacctact ggacattgcc gagcgcatcc aggaggccgg | 780 |

```
cgcgggcctg cgtagcctgg cagagccgtg ggccgacacc accacgccgg ccggccgcat    840
ggtgttgacc gtgttcgccg gcattgccga gttcgagcgt tccctaatca tcgaccgcac    900
ccggagcggg cgcgaggccg ccaaggcccg aggcgtgaag tttggccccc gccctaccct    960
caccccggca cagatcgcgc acgcccgcga gctgatcgac caggaaggcc gcaccgtgaa   1020
agaggcggct gcactgcttg gcgtgcatcg ctcgaccctg taccgcgcac ttgagcgcag   1080
cgaggaagtg acgcccaccg aggccaggcg gcgcggtgcc ttccgtgagg acgcattgac   1140
cgaggccgac gccctggcgg ccgccgagaa tgaacgccaa gaggaacaag catgaaaccg   1200
caccaggacg gccaggacga accgtttttc attaccgaag agatcgaggc ggagatgatc   1260
gcggccgggt acgtgttcga gccgcccgcg cacgtctcaa ccgtgcggct gcatgaaatc   1320
ctggccggtt tgtctgatgc caagctggcg gcctggccgg ccagcttggc cgctgaagaa   1380
accgagcgcc gccgtctaaa aggtgatgt gtatttgagt aaaacagctt gcgtcatgcg   1440
gtcgctgcgt atatgatgcg atgagtaaat aaacaaatac gcaaggggaa cgcatgaagg   1500
ttatcgctgt acttaaccag aaaggcgggt caggcaagac gaccatcgca acccatctag   1560
cccgcgccct gcaactcgcc ggggccgatg ttctgttagt cgattccgat ccccagggca   1620
gtgcccgcga ttgggcggcc gtgcgggaag atcaaccgct aaccgttgtc ggcatcgacc   1680
gcccgacgat tgaccgcgac gtgaaggcca tcggccggcg cgacttcgta gtgatcgacg   1740
gagcgcccca gcggcggac ttggctgtgt ccgcgatcaa ggcagccgac ttcgtgctga   1800
ttccggtgca gccaagccct tacgacatat gggccaccgc cgacctggtg gagctggtta   1860
agcagcgcat tgaggtcacg gatggaaggc tacaagcggc ctttgtcgtg tcgcgggcga   1920
tcaaaggcac gcgcatcggc ggtgaggttg ccgaggcgct ggccgggtac gagctgccca   1980
ttcttgagtc ccgtatcacg cagcgcgtga gctacccagg cactgccgcc gccggcacaa   2040
ccgttcttga atcagaaccc gagggcgacg ctgcccgcga ggtccaggcg ctggccgctg   2100
aaattaaatc aaaactcatt tgagttaatg aggtaaagag aaaatgagca aaagcacaaa   2160
cacgctaagt gccggccgtc cgagcgcacg cagcagcaag gctgcaacgt tggccagcct   2220
ggcagacacg ccagccatga agcgggtcaa ctttcagttg ccggcggagg atcacaccaa   2280
gctgaagatg tacgcggtac gccaaggcaa gaccattacc gagctgctat ctgaatacat   2340
cgcgcagcta ccagagtaaa tgagcaaatg aataaatgag tagatgaatt ttagcggcta   2400
aaggaggcgg catggaaaat caagaacaac caggcaccga cgccgtggaa tgccccatgt   2460
gtggaggaac gggcggttgg ccaggcgtaa gcggctgggt tgtctgccgg ccctgcaatg   2520
gcactggaac cccaagccc gaggaatcgg cgtgacggtc gcaaaccatc cggcccggta   2580
caaatcggcg cggcgctggg tgatgacctg gtggagaagt tgaaggccgc gcaggccgcc   2640
cagcggcaac gcatcgaggc agaagcacgc cccggtgaat cgtggcaagc ggccgctgat   2700
cgaatccgca aagaatcccg gcaaccgccg gcagccggtg cgccgtcgat taggaagccg   2760
cccaagggcg acgagcaacc agattttttc gttccgatgc tctatgacgt gggcacccgc   2820
gatagtcgca gcatcatgga cgtggccgtt ttccgtctgt cgaagcgtga ccgacgagct   2880
ggcgaggtga tccgctacga gcttccagac gggcacgtag aggtttccgc agggccggcc   2940
ggcatggcca gtgtgtggga ttacgacctg gtactgatgg cggtttccca tctaaccgaa   3000
tccatgaacc gataccggga agggaaggga gacaagcccg gccgcgtgtt ccgtccacac   3060
gttgcggacg tactcaagtt ctgccggcga gccgatggcg gaaagcagaa agacgacctg   3120
```

```
gtagaaacct gcattcggtt aaacaccacg cacgttgcca tgcagcgtac gaagaaggcc    3180
aagaacggcc gcctggtgac ggtatccgag ggtgaagcct tgattagccg ctacaagatc    3240
gtaaagagcg aaaccgggcg gccggagtac atcgagatcg agctagctga ttggatgtac    3300
cgcgagatca cagaaggcaa gaacccggac gtgctgacgg ttcaccccga ttactttttg    3360
atcgatcccg gcatcggccg ttttctctac cgcctggcac gccgcgccgc aggcaaggca    3420
gaagccagat ggttgttcaa gacgatctac gaacgcagtg gcagcgccgg agagttcaag    3480
aagttctgtt tcaccgtgcg caagctgatc gggtcaaatg acctgccgga gtacgatttg    3540
aaggaggagg cggggcaggc tggcccgatc ctagtcatgc gctaccgcaa cctgatcgag    3600
ggcgaagcat ccgccggttc ctaatgtacg gagcagatgc tagggcaaat tgccctagca    3660
ggggaaaaag gtcgaaaagg tctctttcct gtggatagca cgtacattgg gaacccaaag    3720
ccgtacattg ggaaccggaa cccgtacatt gggaacccaa agccgtacat tgggaaccgg    3780
tcacacatgt aagtgactga tataaaagag aaaaaaggcg attttccgc ctaaaactct     3840 ttaaaactta ttaaaactct taaaacccgc ctggcctgtg cataactgtc tggccagcgc    3900
acagccgaag agctgcaaaa agcgcctacc cttcggtcgc tgcgctccct acgcccgcc    3960 gcttcgcgtc ggcctatcgc ggccgctggc cgctcaaaaa tggctggcct acggccaggc    4020
aatctaccag ggcgcggaca agccgcgccg tcgccactcg accgccggcg acccgccgca    4080
tccataccgc cagttgttta ccctcacaac gttccagtaa ccgggcatgt tcatcatcag    4140
taacccgtat cgtgagcatc ctctctcgtt tcatcggtat cattacccccc atgaacagaa    4200 attccccctt acacggaggc atcaagtgac caaacaggaa aaaaccgccc ttaacatggc    4260
ccgctttatc agaagccaga cattaacgct tctggagaaa ctcaacgagc tggacgcgga    4320
tgaacaggca gacatctgtg aatcgcttca cgaccacgct gatgagcttt accgcagctg    4380
cctcgcgcgt ttcggtgatg acggtgaaaa cctctgacac atgcagctcc cggagacggt    4440
cacagcttgt ctgtaagcgg atgccgggag cagacaagcc cgtcagggcg cgtcagcggg    4500
tgttggcggg tgtcggggcg cagccatgac ccagtcacgt agcgatagcg gagtgtatac    4560
tggcttaact atgcggcatc agagcagatt gtactgagag tgcaccatat gcggtgtgaa    4620
ataccgcaca gatgcgtaag gagaaaatac cgcatcaggc gctcttccgc ttcctcgctc    4680
actgactcgc tgcgctcggt cgttcggctg cggcgagcgg tatcagctca ctcaaaggcg    4740
gtaatacggt tatccacaga atcagggdat aacgcaggaa agaacatgtg agcaaaaggc    4800
cagcaaaagg ccaggaaccg taaaaaggcc gcgttgctgg cgttttccca taggctccgc    4860
ccccctgacg agcatcacaa aaatcgacgc tcaagtcaga ggtggcgaaa cccgacagga    4920
ctataaagat accaggcgtt tccccctgga agctccctcg tgcgctctcc tgttccgacc    4980
ctgccgctta ccggatacct gtccgccttt ctcccttcgg aagcgtggc gctttctcat     5040 agctcacgct gtaggtatct cagttcggtg taggtcgttc gctccaagct gggctgtgtg    5100
cacgaacccc ccgttcagcc cgaccgctgc gccttatccg gtaactatcg tcttgagtcc    5160
aacccggtaa gacacgactt atcgccactg gcagcagcca ctggtaacag gattagcaga    5220
gcgaggtatg taggcggtgc tacagagttc ttgaagtggt ggcctaacta cggctacact    5280
agaaggacag tatttggtat ctgcgctctg ctgaagccag ttaccttcgg aaaaagagtt    5340
ggtagctctt gatccggcaa acaaaccacc gctggtagcg gtggttttt tgtttgcaag    5400 cagcagatta cgcgcagaaa aaaaggatct caagaagatc ctttgatctt ttctacgggg    5460
tctgacgctc agtggaacga aaactcacgt taagggattt tggtcatgca ttctaggtac    5520
```

```
taaaacaatt catccagtaa aatataatat tttattttct cccaatcagg cttgatcccc    5580
agtaagtcaa aaaatagctc gacatactgt tcttccccga tatccttgat ccggcaaaca    5640
aaccaccgct ggtagcggtg gttttttttgt ttgcaagcag cagattacgc gcagaaaaaa    5700
aggatctcaa gaagatcctt tgatcttttc tacggggtct gacgctcagt ggaacgaaaa    5760
ctcacgttaa gggattttgg tcatgcatga tatatctccc aatttgtgta gggcttatta    5820
tgcacgctta aaaataataa agcagactt gacctgatag tttggctgtg agcaattatg    5880
tgcttagtgc atctaatcgc ttgagttaac gccggcgaag cggcgtcggc ttgaacgaat    5940
ttctagctag acattatttg ccgactacct tggtgatctc gcctttcacg tagtggacaa    6000
attcttccaa ctgatctgcg cgcgaggcca agcgatcttc ttcttgtcca agataagcct    6060
gtctagcttc aagtatgacg ggctgatact gggccggcag gcgctccatt gcccagtcgg    6120
cagcgacatc cttcggcgcg attttgccgg ttactgcgct gtaccaaatg cgggacaacg    6180
taagcactac atttcgctca tcgccagccc agtcgggcgg cgagttccat agcgttaagg    6240
tttcatttag cgcctcaaat agatcctgtt caggaaccgg atcaaagagt tcctccgccg    6300
ctggacctac caaggcaacg ctatgttctc ttgcttttgt cagcaagata gccagatcaa    6360
tgtcgatcgt ggctggctcg aagatacctg caagaatgtc attgcgctgc cattctccaa    6420
attgcagttc gcgcttagct ggataacgcc acggaatgat gtcgtcgtgc acaacaatgg    6480
tgacttctac agcgcggaga atctcgctct ctccagggga agccgaagtt ccaaaaggt    6540
cgttgatcaa agctcgccgc gttgtttcat caagccttac ggtcaccgta accagcaaat    6600
caatatcact gtgtggcttc aggccgccat ccactgcgga gccgtacaaa tgtacggcca    6660
gcaacgtcgg ttcgagatgg cgctcgatga cgccaactac ctctgatagt tgagtcgata    6720
cttcggcgat caccgcttcc cccatgatgt ttaactttgt tttagggcga ctgccctgct    6780
gcgtaacatc gttgctgctc cataacatca aacatcgacc cacggcgtaa cgcgcttgct    6840
gcttggatgc ccgaggcata gactgtaccc caaaaaaaca tgtcataaca gaagccatg    6900
aaaaccgcca ctgcgccgtt accaccgctg cgttcggtca aggttctgga ccagttgcgt    6960
gacggcagtt acgctacttg cattacagct tacgaaccga acgaggctta tgtccactgg    7020
gttcgtgccc gaattgatca caggcagcaa cgctctgtca tcgttacaat caacatgcta    7080
ccctccgcga gatcatccgt gtttcaaacc cggcagctta gttgccgttc ttccgaatag    7140
catcggtaac atgagcaaag tctgccgcct acaacggct ctcccgctga cgccgtcccg    7200
gactgatggg ctgcctgtat cgagtggtga ttttgtgccg agctgccggt cggggagctg    7260
ttggctggct ggtggcagga tatattgtgg tgtaaacaaa ttgacgctta gacaacttaa    7320
taacacattg cggaccgcgg aacctatctt tattcatgaa agaaaggaga acaatgagag    7380
gggggatttt aaagggttat gaataattaa ctaccgagag gctcgttcaa aaaatgtgaa    7440
atatttctcc attttcgcta atatttctca cactccgaag tccttcattc cccatccaaa    7500
caaagtctta aggggtgggt catgactcat taactaacga gaggctcatt cactcacata    7560
acaacatcat tatgtgacaa cacaccaagt gtacgtttgt tctaataaat agtaagtacc    7620
agacaaaaca acacaagaca acaactcaag acaaatatag acaaaaaaaa ctattttgat    7680
attttagaca acttgcatgt gagacataaa atacttgtgt tgtggtttaa cgagggatac    7740
aaatttcagt ttttgtcttg tctcttgctt caaattatc ttgttcacaa aagagtttta    7800
caaatcaaac aataaacaaa tggattctca tgttcttcat ttttttagag aaataatatt    7860
```

```
tgaacatcat ttttagaca atttttatc aatcttcttt cttagactca cattatattc    7920
ttattctctt tctttttttc tcaattgttt ttgagcggta acaaaaattg taagttgtca    7980
catatagtta tacaaatatc actattcttt ttttatgatg tcaaacgcca cccgttatat    8040
ataatctcct agagccttct agaaacgtaa tcgcatatgt agtacgaaaa ttgtcgtagt    8100
tgaccacctt gattttacac gtggcaaata tttactagta gatgtagatt aggaggctat    8160
tttcgtaatt gagtcggcac atccttgata taaatacaac aaccattgtt ttcatcgtcg    8220
ttacctattc gctcgcaatc gcaaagcaaa atttccaaac gctcttttct ctcttcttcg    8280
acaaatctac gattcattca attcaggcca tggacctgca tctaattttc ggtccaactt    8340
gcacaggaaa gacgacgacc gcgatagctc ttgcccagca gacagggctt ccagtccttt    8400
cgcttgatcg ggtccaatgc tgtcctcaac tatcaaccgg aagcggacga ccaacagtgg    8460
aagaactgaa aggaacgacg cgtctctacc ttgatgatcg gcctctggtg gagggtatca    8520
tcgcagccaa gcaagctcat cataggctga tcgaggaggt gtataatcat gaggccaacg    8580
gcgggcttat tcttgaggga ggatccacct cgttgctcaa ctgcatggcg cgaaacagct    8640
attggagtgc agattttcgt tggcatatta ttcgccacaa gttacccgac caagagacct    8700
tcatgaaagc ggccaaggcc agagttaagc agatgttgca ccccgctgca ggccattcta    8760
ttattcaaga gttggtttat cttttggaatg aacctcggct gaggcccatt ctgaaagaga    8820
tcgatggata tcgatatgcc atgttgtttg ctagccagaa ccagatcacg gcagatatgc    8880
tattgcagct tgacgcaaat atggaaggta agttgattaa tgggatcgct caggagtatt    8940
tcatccatgc gcgccaacag gaacagaaat tcccccaagt taacgcagcc gctttcgacg    9000
gattcgaagg tcatccgttc ggaatgtatt aggttacgcc agccctgcgt cgcacctgtc    9060
ttcatctgga taagatgttc gtaattgttt ttggctttgt cctgttgtgg cagggcggca    9120
aatacttccg acaatccatc gtgtcttcaa actttatgct ggtgaacaag tcttagtttc    9180
cacgaaagta ttatgttaaa ttttaaaatt tcgatgtata atgtggctat aattgtaaaa    9240
ataaactatc gtaagtgtgc gtgttatgta taatttgtct aaatgtttaa tatatatcat    9300
agaacgcaat aaatattaaa tatagcgctt ttatgaaata taaatacatc attacaagtt    9360
gtttatattt cgggtggact agttttaat gtttagcaaa tgtcctatca gttttctctt    9420
tttgtcgaac ggtaatttag agttttttt gctatatgga ttttcgtttt tgatgtatgt    9480
gacaaccctc gggattgttg atttatttca aaactaagag ttttgctta ttgttctcgt    9540
ctattttgga tatcaatctt agtttatat cttttctagt tctctacgtg ttaaatgttc    9600
aacacactag caatttggct gcagcgtatg gattatggaa ctatcaagtc tgtgggatcg    9660
ataaatatgc ttctcaggaa tttgagattt tacagtcttt atgctcattg ggttgagtat    9720
aatatagtaa aaaatagga attctatccg cggtgatcac aggcagcaac gctctgtcat    9780
cgttacaatc aacatgctac cctccgcgag atcatccgtg tttcaaaccc ggcagcttag    9840
ttgccgttct tccgaatagc atcggtaaca tgagcaaagt ctgccgcctt acaacggctc    9900
tcccgctgac gccgtcccgg actgatgggc tgcctgtatc gagtggtgat tttgtgccga    9960
gctgccggtc ggggagctgt tggctggctg gaagctttgg ctggaacctt ggcggcagga   10020
tgtatacaga ggtatacaat tttatattac atttatattt gtgttaattc attgaatttt   10080
cacttttatt ttttactttg ataatcaact gtgtaaagaa ttatttgaaa aatatatata   10140
atttatagaa ttttttttg ttatggggcc c                                   10171
```

```
<210> SEQ ID NO 6
<211> LENGTH: 780
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 6
atgaagacta atcttttct ctttctcatc ttttcacttc tcctatcatt atcctcggcc        60
gaattcagta aaggagaaga acttttaca ggtgttgttc ccatattagt tgaattagac       120
ggcgatgtaa atggacataa attttcagtt tcaggagaag gagaaggtga cgcaacatac      180
ggcaaattaa cactcaagtt tatatgtaca acaggaaaac tcccagttcc ttggcccaca      240
ttagtaacaa cattaactta cggagtacaa tgtttcagta gatacccaga ccatatgaaa      300
agacatgatt tttttaaatc agcaatgcca gaaggatacg ttcaggaaag gacaatattt      360
tttaaagatg acggaaatta taagacaaga gcagaagtta aatttgaagg agatacatta      420
gtaaacagaa ttgaattgaa aggaatagat tttaaagaag acggaaatat cttaggacac      480
aaacttgaat ataattataa ctcacacaat gtttatatca tggcagacaa acagaaaaac      540
ggaatcaaag ctaatttcaa aacaagacac aatattgaag acggaggagt acaattagca      600
gaccactatc aacaaaatac ccctatagga gatggcccag ttttacttcc agacaatcat      660
taccttagta cacaatcagc ccttagtaaa gaccccaacg aaaaaagaga ccatatggtg      720
ctattagaat ttgttacagc cgccggtatc acacatggaa tggatgaatt atataaataa      780

<210> SEQ ID NO 7
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: a or u

<400> SEQUENCE: 7 uuuuuanuuu                                                              10
```

PRECISE CUTTING

This regular U.S. utility application claims priority to U.S. Provisional Application Ser. No. 60/702,638, which was filed on Jul. 27, 2005, and which is incorporated herein by reference in its entirety.

FIELD OF THE INVENTION

The present invention provides methods for plant transformation. One such method entails (i) making an excision in a seedling at the point where the two cotyledons meet, (ii) exposing the resulting decapitated seedling to a transforming bacteria carrying a transfer DNA such as *Agrobacterium*, and (iii) screening new shoots that emerge from the cut surface, or plants or offspring derived thereof, for the presence of at least part of the transfer DNA.

BACKGROUND

The forage legume alfalfa (*Medicago sativa*) has high nutritional value and low fiber content and, consequently, is an important dairy feed. Traits such as these, as well as others, can be improved upon by conventional plant transformation techniques. In this regard, conventional methods of transforming alfalfa typically rely on infecting alfalfa leaf explants from highly regenerable clones to produce transformed alfalfa plants (Bingham, *Crop Sci.*, 31:1098, 1991; Austin, et al., *Euphytica*, 85: 381-393, 1995). These methods, however, require multiple manipulative steps, such selection, somatic embryogenesis, and regeneration, which prove labor-intensive, time consuming, and costly.

Moreover, conventional transformation methods typically introduce foreign DNA into the alfalfa genome permanently. Such foreign DNA generally includes selectable marker genes, extended *Agrobacterium* T-DNA border regions, and regulatory elements from viral and bacterial origins. The presence of foreign DNA in foodstuffs destined for human consumption may cause concern to some. For this reason, Rommens et al. in U.S. patent publication serial No. 2003/0221213, were the first to propose the all native approach to genetic engineering. In this approach, only DNA from the genome of the organism of interest, or DNA accessible to the organism of interest through naturally breeding, is introduced via genetic engineering techniques. Plants obtained through this new plant breeding process do not contain foreign nucleic acid but only contain nucleic acid from the plant species selected for transformation, or plants that are sexually compatible with the selected plant species. Potato plants (*Solanum tuberosum*) that display enhanced black spot bruise tolerance represent plants generated through genetic engineering with only native DNA obtained from the potato genome. The tools that were developed for this purpose include efficient marker-free transformation and replacement of foreign genetic elements involved in gene transfer and expression by DNA sequences from the target plant species.

Interestingly, various important improvements for alfalfa may be accomplished by modifying the expression of endogenous genes and would, thus, not require foreign genes. For instance, it has been shown that reduced expression of endogenous caffeic acid o-methyltransferase (Comt) or caffeoyl CoA 3-O-methyltransferase (Ccomt) genes triggered up to 30% decreases in lignin content and consequently enhanced the nutritional value of alfalfa forage (Guo et al., Plant Cell 13: 73-88, 2001; Guo et al., Transgenic Res 10: 457-464, 2001), at the same time also reducing the amount of waste manure by-product. The availability of all-native DNA transformation methods would make it possible to improve the alfalfa crop while addressing key public concerns. The development of such methods is described herein, as is the exploitation of these methods to reduce lignin content in intragenic alfalfa plants.

SUMMARY

One aspect of the present invention is a method for transforming a plant, comprising (a) cutting a seedling at a precise location, (b) vortexing the seedling for a period of time in a suspension of bacterium that contains a transformation plasmid, which carries a desired transfer DNA, (c) retrieving the seedling from the suspension after the period of time and incubating the seedling until at least one new shoot emerges from it, (d) cultivating a plant from the seedling, and (e) determining whether the plant is stably transformed with the desired transfer DNA or a part thereof.

The method may further comprise growing a plant that is stably transformed with the desired transfer DNA or a part thereof so that it produces seed, and then screening progeny plants grown from those seeds to identify those progeny plants that also are stably transformed with the desired transfer DNA or the part thereof.

In one embodiment, the cotyledons are excised from the seedling at the location on the seedling where the base of each cotyledon meet. In one embodiment, the seedling has two cotyledons. In another embodiment, the two cotyledons are excised from the seedling at the point where the two cotyledons meet.

In another embodiment, the above-ground tissues of the plant grown from the seedling are stably transformed with the desired transfer DNA or the part thereof.

One aspect of the present invention is a method for transforming a plant, comprising the steps of (a) making an excision in a seedling at the point where the two cotyledons meet, (b) vortexing said decapitated seedling in a suspension of bacterium that contains a transformation plasmid, which carries a desired transfer DNA, (c) allowing emergence of at least one new shoot from the cut surface and cultivating a plant, (d) identifying a plant with stably transformed above-ground tissues, (e) allowing this plant to produce seed, and (f) screening the progeny for stably transformed plants.

In one embodiment, the transformation plasmid used in such methods comprises a desired transfer DNA that consists essentially of DNA sequences that are native to either the species of the plant that is to be transformed or species that are sexually compatible with the target species.

One aspect of the present invention provides a method for producing a transgenic plant, comprising (a) exposing a seedling to at least one bacterium strain that contains a transformation plasmid carrying a desired polynucleotide, wherein all tissues above the position where the two cotyledons meet have been excised; (b) cultivating the decapitated and infected seedling to produce at least one new shoot; (c) identifying whether the desired polynucleotide is integrated into the genome of at least one cell of either the shoot or the above-ground tissues of a plant derived from this shoot.

In a preferred embodiment, the seedling is obtained by allowing a sterile seed to germinate for about one to about eight days.

In another embodiment of this method, an excision is made in a part of the seedling. That is, a part of the seedling is cut in such a way that the seedling is able to produce a new shoot at the cut surface. This excision removes the tissues above the position where the two or more cotyledons meet and includes at least part of both the cotyledons and initial unifoliate leaves. In a preferred embodiment, therefore, the seedling is cut at the site where the cotyledons meet so that the cotyledons and the initial unifoliate leaves are chopped away or otherwise "excised" from the seedling.

According to the present invention, it may be desirable to excise the two cotyledons of alfalfa at their base where they each meet, which is typically at the thickest region of the stem. Excisions that are made too far below that region in the stem could prevent or hamper new shoot formation, while slicing the cotyledons off at a point too high above the base of the cotyledons could reduce the extent of stable transformation of the seedling with the desired DNA.

In one embodiment, the seedling can be of any plant species. In one embodiment, the seedling is from a legume. In one embodiment, the legume is selected from the group consisting of alfalfa, pea, soybean, peanut, chickpea, and barrel medic. In a preferred embodiment, the seedling is from alfalfa, canola, or sugarbeet. In a most preferred embodiment, the seedling is from alfalfa.

In another preferred embodiment, the seedling is from another dicotyledonous plant, such as cotton, tobacco, tomato, potato, sugar beet, broccoli, cassava, sweet potato, pepper, poinsettia, soybean, carrot, strawberry, lettuce, oak, maple, walnut, rose, mint, squash, daisy, geranium, or cactus.

In one embodiment, the bacterium that contains the transformation plasmid is a bacterium of *Agrobacterium, Rhizobium,* or *Phyllobacterium*. In a further embodiment, the bacterium is selected from the group consisting of *Agrobacterium tumefaciens, Rhizobium trifolii, Rhizobium leguminosarum, Phyllobacterium myrsinacearum, Sinorhizobium meliloti,* and *Mesorhizobium loti*.

In one embodiment, the cut seedling is exposed to the bacterium by immersing it in a suspension of the bacterium. Once the seedling is so immersed, the suspension may be vortexed but not sonicated. In this regard, a vessel that contains the present bacterium and seedling is vortexed for a length of time.

In one embodiment, the length of time of vortexing is not fixed and can be determined empirically. For instance, the vessel containing the bacterium suspension and immersed seedling may be vortexed for 1, 5, 10, 15, 20, 30, 60 minutes, or more than 60 minutes. The vortexing step should not prevent emergence of new shoots from the cut surface and should yield a high frequency of stable transformation of new shoots.

In a preferred embodiment, the transformation plasmid that carries the desired polynucleotide contains regulatory elements that are native to the plant species that is selected for transformation. That is, the desired polynucleotide is operably linked to at least one of a promoter, enhancer, or terminator that is endogenous to the species of the plant to be transformed. For instance, if the seedling is a germinating seedling from alfalfa, then the desired polynucleotide may be operably linked to a least one of a promoter, enhancer, or terminator that naturally occurs in, e.g., is native to, the alfalfa genome.

In one embodiment, all of the genetic elements that are ultimately transferred from the transformation plasmid to the plant genome are native to the plant species that is selected for transformation. In that embodiment, the promoter, enhancer, and terminator, if present, as well as the desired polynucleotide, are all endogenous to the plant species that is to be transformed. In one embodiment, at least one, if not all, of the genetic elements that are transferred from the plasmid to the plant genome are isolated from the same plant, or from a plant from the same species as the plant species that is selected for transformation, or from a plant that belongs to a species that is sexually interfertile with the species that is to be transformed.

In one embodiment, therefore, a native genetic element is a nucleic acid that naturally exists in, originates from, or belongs to the genome of a plant that is to be transformed. Thus, any nucleic acid, gene, polynucleotide, genomic DNA, DNA, RNA, mRNA, or cDNA molecule that is isolated either from the genome of a plant or plant species that is to be transformed, or is isolated from a plant or species that is sexually compatible, or interfertile with the plant species that is to be transformed, is "native" to, i.e., indigenous to, the plant species. In other words, a native genetic element represents all genetic material that is accessible to plant breeders for the improvement of plants through classical plant breeding. For instance, native DNA incorporated into cultivated alfalfa can be derived from any genotype of alfalfa or any genotype of a wild alfalfa species that is sexually compatible with alfalfa.

Any variants of a native nucleic acid also are considered native in accordance with the present invention. In another embodiment, therefore, a native nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence.

In another embodiment, a native nucleic acid isolated from a plant may also encode a variant of the naturally occurring plant protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in amino acid sequence to the unmodified, native protein expressed in the plant from which the nucleic acid was isolated.

Accordingly, in one embodiment, the present method entails limiting the number of non-native genetic elements into the transformed plant. Ideally, in one embodiment, the method does not introduce any foreign nucleic acids into the genome of the plant. In one embodiment, a foreign nucleic acid is one that is derived from non-plant organisms, or derived from a plant that is not the same species as the plant to be transformed or is not derived from a plant that is not interfertile with the plant to be transformed, does not belong to the species of the target plant. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product. According to the present invention, a most desired transgenic plant is one that contains minimal, if any, foreign nucleic acids integrated into its genome. The present invention also encompasses transgenic plants that do contain non-plant species nucleic acids in their genomes.

In another embodiment, the expression of the desired polynucleotide in the stably transformed plant confers a trait to the plant selected from the group consisting of increased drought tolerance, reduced height, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved taste, improved texture, decreased phosphate content, increased germination, increased micronutrient uptake, improved starch composition, improved flower longevity, and production of novel proteins or peptides.

In a preferred embodiment, the desired polynucleotide of the present invention is selected from the group consisting of a gene or part thereof, the 5'-untranslated "leader" region of the gene, the 3'-untranslated "trailer" region of the gene, or the promoter associated with the gene.

In a preferred embodiment, the gene encodes a protein that is selected from the group consisting of an antifungal, a nutritional peptide or protein, a transcription factor, a receptor that binds to pathogen-derived ligands, a hemoglobin, an oxidase, an enzyme of the lignin biosynthesis pathway, an enzyme of the fatty acid biosynthesis pathway, an enzyme of industrial value, a protein involved in yield, or an antigen.

In one embodiment, the step of identifying whether the desired polynucleotide is integrated into the plant genome can be accomplished, for example, by comparing one or more traits between the plant obtained from the cut and infected seedling or a progeny thereof and a wild-type plant of the same species, where a difference in a particular trait between the wild-type and obtained plants indicates that the desired polynucleotide is integrated into the plant genome.

Alternatively, the polymerase chain reaction may be employed to amplify nucleic acids extracted from the obtained plant or progeny thereof to determine whether all or part of the desired polynucleotide can be isolated therefrom.

Similarly, a nucleic probe may be employed in a Northern or Southern blot, for instance, to identify the presence of the desired polynucleotide in the plant genome or of its RNA transcript from a cell extract.

In another embodiment, methods such as ELISA may be employed to identify the protein product, if any, of the desired polynucleotide in a protein extract of the obtain plant or its progeny.

A method for determining whether the desired polynucleotide is integrated into the plant genome may entail assaying the cell for downstream effects of expression of the desired polynucleotide. For instance, one may determine whether the expression level of an endogenous gene is altered in comparison to the expression level of the same gene in a wild-type plant of the same species. The amount or presence or absence of the gene's RNA transcript or the gene's protein product is indicative of the gene's expression level.

Hence, one aspect of the present invention is a method for transforming a plant, comprising the steps of (a) making an excision in a seedling at the point where two cotyledons meet so that the seedling is able to produce a new shoot at the cut surface, (b) vortexing said cut seedling in a suspension of bacterium that contains a transformation plasmid comprising a desired transfer DNA that consists essentially of native DNA sequences, (c) cultivating a plant obtained from said cut seedling, and (d) identifying a plant containing above-ground tissues that are stably transformed with said native DNA and lacking plasmid backbone DNA sequences.

In one embodiment, the seedling is from alfalfa, canola, or sugarbeet. In a preferred embodiment, the seedling is from alfalfa.

In another embodiment, the seedling is obtained by germinating a sterile seed for about one to about eight days.

In another embodiment, the excision that is made on the seedling is made to remove the cotyledons. In a preferred embodiment, the excision is made at the position where the two cotyledons meet. In alfalfa, this position represents the thickest region of the stem.

In one embodiment, the step of vortexing said cut seedling in a suspension of bacteria entails vortexing the seedling in the bacterium suspension.

In another embodiment, the desired DNA region is operably linked to at least one of the nucleotide sequences selected from the group consisting of SEQ ID NOs.: 2, 3, 4, and 5.

In a further embodiment, the transformation plasmid comprises an *E. Coli* replication-associated rom gene. In one embodiment, the rom gene comprises the sequence depicted in SEQ ID NO: 1.

In another embodiment, the suspension of bacterium comprises a chemical that stimulates transformation such as acetosyringone.

In another embodiment, the bacterium is selected from the group consisting of *Agrobacterium, Rhizobium*, and *Phyllobacterium*. In a particular embodiment, the bacterium is selected from the group consisting of *Agrobacterium tumefaciens, Rhizobium trifolii, Rhizobium leguminosarum, Phyllobacterium myrsinacearum, Sinorhizobium meliloti*, and *Mesorhizobium loti*.

In one embodiment, the method may further comprise producing a progeny plant from the transgenic plant.

The present invention also provides a progeny plant obtained from the method described herein. In one embodiment, the progeny plant is from a transformed alfalfa, canola, or sugarbeet plant. In one embodiment, the progeny plant is a progeny of a transformed alfalfa plant obtained from any of the methods described herein.

The present invention also provides a method for transforming alfalfa, comprising (a) making an excision in a seedling at the point where the two cotyledons meet, (b) vortexing the decapitated seedling in a suspension of *Agrobacterium* that contains a transformation plasmid comprising a desired transfer DNA that consists essentially of native DNA sequences, and (c) screening new shoots that emerge from the cut surface, or plants or offspring derived thereof, for the presence of at least part of said native DNA.

Also provided by the present invention is an isolated polynucleotide, comprising the sequence of any one of SEQ ID NOs.: 2, 3, or 4, wherein said polynucleotide drives the expression of another polynucleotide to which it is operably linked.

Also provided is an isolated polynucleotide, comprising the sequence of SEQ ID NO: 5, wherein the polynucleotide terminates expression of another polynucleotide to which it is operably linked.

The present invention also is drawn to a method for transforming a plant, comprising (a) cutting the seedling at the intersection of the stem where the cotyledons of the seedling meet, (b) vortexing the cut seedling in a suspension of bacterium, which comprises a transformation plasmid that carries a desired transfer DNA (c) cultivating at least one shoot from the seedling, (d) growing a plant from the shoot, and (e) identifying a plant that is stably transformed with the desired transfer DNA, wherein such a plant is a transformed plant.

In one embodiment, the seedling is a seedling from alfalfa, pea, soybean, peanut, chickpea, canola, sugarbeet, clover, cotton, and barrel medic. In a preferred embodiment, the seedling is an alfalfa seedling.

In one embodiment, both cotyledons of the cotyledon are excised from the seedling at the thickest part of the seedling stem where the cotyledons meet.

In one embodiment, the desired transfer DNA is a P-DNA or a T-DNA that consists essentially of only nucleic acid sequences that are native to the genome of the seedling's species or native to a species that is sexually compatible with the seedling.

In another embodiment, the method further comprises (a) growing the plant to produce seeds, (b) growing progeny plants from those seeds, and (c) identifying those progeny plants that are stably transformed with the desired transfer DNA, wherein such plants are transformed progeny plants.

In one embodiment, the seedling is germinated for one to eight days prior to cotyledon removal.

In another embodiment, the bacterium is selected from the group consisting of *Agrobacterium, Rhizobium*, and *Phyllobacterium*. In one embodiment, the bacterium is selected from the group consisting of *Agrobacterium tumefaciens, Rhizobium trifolii, Rhizobium leguminosarum, Phyllobacterium myrsinacearum, Sinorhizobium meliloti,* and *Mesorhizobium loti*.

In a further embodiment, the desired transfer DNA comprises an expression cassette that comprises a desired alfalfa polynucleotide operably linked to a PetE promoter and an E9 terminator. In one particular embodiment, the transformation plasmid comprises the sequence depicted in SEQ ID NO: 5.

The present invention also is drawn to a plant that is obtained from this or any method described herein.

The present invention also encompasses a progeny plant obtained from this or any method described herein.

According to the present invention, in one embodiment, a plant obtained from any of the methods described herein, is not stably transformed with a marker gene.

These, as well as other embodiments, are described in more detail below.

DETAILED DESCRIPTION

Figure 1:
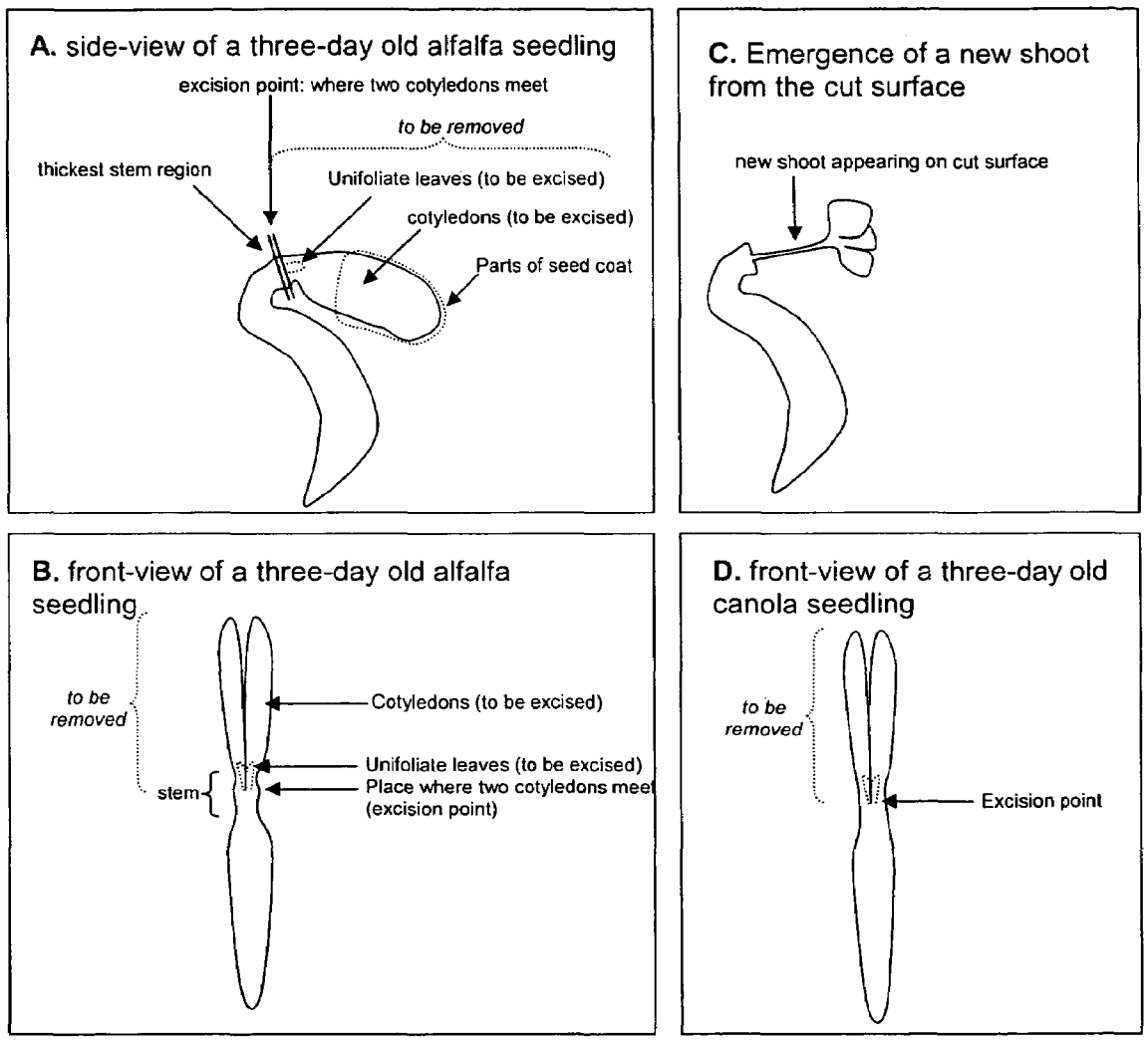
FIG. 1. Precise Cutting. Excision point in a three-day old alfalfa seedling (A and B). Appearance of a new shoot at the cut surface of a decapitated seedling (C). Excision point in a two-day old canola seedling (D).

The present invention provides methods for enhancing plant transformation. One such method entails making an incision in the selected seedling at a desired site and then exposing that site or the entire tissue to a transforming bacteria, such as *Agrobacterium*.

Unless defined otherwise, all technical and scientific terms used herein have the same meaning as commonly understood by one of ordinary skill in the art to which this invention belongs. Generally, the nomenclature used herein, and the laboratory procedures in cell culture, molecular genetics, and nucleic acid chemistry and hybridization described herein, are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology disclosed, for example, in *Molecular cloning a laboratory manual*, 2d ed., Cold Spring Harbor Laboratory Press, Cold Spring Harbor, N.Y. (1989), and *Current protocols in molecular biology*, John Wiley & Sons, Baltimore, Md. (1989).

Definitions

Backbone: nucleic acid sequence of a binary vector that excludes the T-DNA or P-DNA sequence intended for transfer.

Bacteria species for transformation: bacteria species and strains other than those of *Agrobacterium*, e.g., *Agrobacterium tumefaciens*, can be used to transform a plant according to the present invention. For instance, any genera within the family Rhizobiaceae can be used in place of *Agrobacterium* to transform a plant. For instance, members of the *Rhizobium* and *Phyllobacterium* genera can be used to transform a plant according to the present invention. Examples include, but are not limited to, *Rhizobium trifolii, Rhizobium leguminosarum, Phyllobacterium myrsinacearum, Sinorhizobium meliloti, Mesorhizobium loti* bacterial strains, which can be used to transform a plant according to the present invention. See Broothaerts et al., Nature, 433, pp. 629-633, 2005, which is incorporated herein by reference.

Border and Border-like sequences: "border sequences" are specific *Agrobacterium*-derived sequences. Typically, a left border sequence and a right border sequence flank a T-DNA and they both function as recognition sites for virD2-catalyzed nicking reactions. Such activity releases nucleic acid that is positioned between such borders. See Table 2 below for examples of border sequences. The released nucleic acid, complexed with virD2 and virE2, is targeted to plant cell nuclei where the nucleic acid is often integrated into the genome of the plant cell. Usually, two border sequences, a left-border and a right-border, are used to integrate a nucleotide sequence that is located between them into another nucleotide sequence. It is also possible to use only one border, or more than two borders, to accomplish integration of a desired nucleic acid in such fashion.

According to the present invention, a "border-like" sequence is isolated from the selected plant species that is to be modified, or from a plant that is sexually-compatible with the plant species to be modified, and functions like the border sequences of *Agrobacterium*. That is, a border-like sequence of the present invention promotes and facilitates the integration of a polynucleotide to which it is linked. A plant-DNA, i.e., P-DNA, of the present invention preferably contains border-like sequences.

A border-like sequence of a P-DNA is between 5-100 bp in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length.

The border-like sequences of the present invention can be isolated from any plant, such as from potato and wheat. Thus, a P-DNA left and right border sequences of use for the present invention are isolated from and/or native to the genome of a plant that is to be modified. A P-DNA border-like sequence is not identical in nucleotide sequence to any known *Agrobacterium*-derived T-DNA border sequence. Thus, a P-DNA border-like sequence may possess 1, 2, 3, 4, 5, 6, 7, 8, 9, 10, 11, 12, 13, 14, 15, 16, 17, 18, 19, 20, or more nucleotides that are different from a T-DNA border sequence from an *Agrobacterium* species, such as *Agrobacterium tumefaciens* or *Agrobacterium rhizogenes*. That is, a P-DNA border, or a border-like sequence of the present invention has at least 95%, at least 90%, at least 80%, at least 75%, at least 70%, at least 60% or at least 50% sequence identity with a T-DNA border sequence from an *Agrobacterium* species, such as *Agrobacterium tumefaciens* or *Agrobacterium rhizogenes*, but not 100% sequence identity. As used herein, the descriptive terms "P-DNA border" and "P-DNA border-like" are exchangeable.

A native P-DNA border sequence is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51% or 50% similar in nucleotide sequence to a *Agrobacterium* a T-DNA border sequence. A border-like sequence can, therefore, be isolated from a plant genome and be modified or mutated to change the efficiency by which they are capable of integrating a nucleotide sequence into another nucleotide sequence. Other polynucleotide sequences may be added to or incorporated within a border-like sequence of the present invention. Thus, a P-DNA left border or a P-DNA right border may be modified so as to possess 5'- and 3'- multiple cloning sites, or additional restriction sites. A P-DNA border sequence may be modified to increase the likelihood that backbone DNA from the accompanying vector is not integrated into the plant genome.

Cotyledons: a cotyledon represents the first leaves to appear after a seed germinates. The cotyledon contain or has access to stored food reserves in the seed. A cotyledon is the foliar portion of the embryo as found in the seed. The number of cotyledons present in a seedling has traditionally been used to classify angiosperms. Species with one cotyledon are monocotyledonous, while species with two embryonic leaves are dicotyledonous. The cotyledon of grasses and monocotyledons is composed of a scutellum and a coleoptile. The scutellum is a tissue within the seed that is absorbs food from the endosperm. The coleoptile is a protective cap that covers the plumule (precursor to the stem and leaves of the plant). Gymnosperm seedlings typically have numerous cotyledonous.

Decapitated seedling: the present invention contemplates the transformation of a "decapitated" seedling. A decapitated seedling is a seedling that has been cut and infected with a transforming bacterium carrying a transformation vector. For instance, a decapitated seedling may be one that was excised at the point where the two cotyledons meet to remove both cotyledons and initial true leaves and to allow emergence of a new shoot from the cut surface. In alfalfa, the excision point is at the thickest part of the stem segment. Excisions that are made too low prevent new shoot formation, whereas excisions that are too high limit stable transformation.

Desired DNA region: the present invention contemplates transforming a plant cell with any desired DNA region or polynucleotide. The DNA region may comprise one or more distinct polynucleotides. For instance, the DNA region may comprise a desired gene of interest that is operably linked to a promoter and a terminator. Hence, the DNA region, in this case, comprises a gene and regulatory elements. If it is placed within a transfer-DNA cassette of a transformation vector, then all or part of the DNA region may be integrated into the plant cell genome. The integration event may yield a stable or transient transformation event. That is, all or part of the DNA region may be stably integrated into the plant cell genome so that it can be transmitted through subsequent generations of the cell and plant.

All or some of the distinct polynucleotides within the desired DNA region may be native to the plant species to be transformed. Put another way, the desired DNA region may or may not contain foreign DNA.

Excision: according to the present invention, a seedling may be cut in such a way that a piece of the seedling is excised away from the bulk of the seedling, thereby exposing an inner surface of the seedling. The cells of that exposed surface are more amenable, therefore, to bacterium inoculation. In the case of a germinating seedling, therefore, it may be desirable to completely remove the cotyledon thereby to expose germ line or regenerable cells that are ready for inoculation with a bacterium suspension in accordance with the present vortexing protocols described herein.

According to the present invention, it can be desirable to excise a part of, or all of, a germinating seedling cotyledon. Either the remaining part of the seedling can then be exposed to a transformation bacterium, such as *Agrobacterium*, or the portion that has been excised can be subject to transformation.

Thus, it is conceivable that once the cotyledon, for instance, or a part of it, has been excised from a germinating seedling that the cotyledon or part thereof is actually placed into a suspension of *Agrobacterium* or another transformation bacteria suspension, and vortexed according to the present invention.

Hence the present invention contemplates transformation of both the excised portion of the seedling as well as the remaining bulk of the seedling.

Foreign: "foreign," with respect to a nucleic acid, means that that nucleic acid is derived from non-plant organisms, or derived from a plant that is not the same species as the plant to be transformed or is not derived from a plant that is not interfertile with the plant to be transformed, does not belong to the species of the target plant. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product. According to the present invention, a desired transgenic plant is one that does not contain any foreign nucleic acids integrated into its genome.

Native genetic elements, on the other hand, can be incorporated and integrated into a selected plant species genome according to the present invention. Native genetic elements are isolated from plants that belong to the selected plant species or from plants that are sexually compatible with the selected plant species. For instance, native DNA incorporated into cultivated potato (*Solanum tuberosum*) can be derived from any genotype of *S. tuberosum* or any genotype of a wild potato species that is sexually compatible with *S. tuberosum* (e.g., *S. demissum*).

Germination: process of incubating a seed in a moist or wet environment to allow emergence of a seedling. For instance, a seed can be placed on agar or on wet sand. The time of incubation equals the germination time.

Meristem: undifferentiated tissue from which new cells are formed, as at the tip of a stem or root. Meristem cloning is the artificial propagation of a plant using cells taken from the meristem of a parent plant and yielding genetically identical offspring.

Native: a "native" genetic element refers to a nucleic acid that naturally exists in, orginates from, or belongs to the genome of a plant that is to be transformed. Thus, any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleic acid also are considered "native" in accordance with the present invention. In this respect, a "native" nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence.

A "native" nucleic acid isolated from a plant may also encode a variant of the naturally occurring protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in amino acid sequence to the unmodified, native protein expressed in the plant from which the nucleic acid was isolated.

Naturally occurring nucleic acid: this phrase means that the nucleic acid is found within the genome of a selected plant species and may be a DNA molecule or an RNA molecule. The sequence of a restriction site that is normally present in the genome of a plant species can be engineered into an exogenous DNA molecule, such as a vector or oligonucleotide, even though that restriction site was not physically isolated from that genome. Thus, the present invention permits the synthetic creation of a nucleotide sequence, such as a restriction enzyme recognition sequence, so long as that sequence is naturally occurring in the genome of the selected plant species or in a plant that is sexually compatible with the selected plant species that is to be transformed.

Operably linked: combining two or more molecules in such a fashion that in combination they function properly in a plant cell. For instance, a promoter is operably linked to a structural gene when the promoter controls transcription of the structural gene.

P-DNA: according to the present invention, P-DNA ("plant-DNA") is isolated from a plant genome and comprises at each end, or at only one end, a T-DNA border-like sequence. The border-like sequence preferably shares at least 50%, at least 60%, at least 70%, at least 75%, at least 80%, at least 90% or at least 95%, but less than 100% sequence identity, with a T-DNA border sequence from an *Agrobacterium* species, such as *Agrobacterium tumefaciens* or *Agrobacterium rhizogenes*. Thus, P-DNAs can be used instead of T-DNAs to transfer a nucleotide sequence from *Agrobacterium* to another polynucleotide sequence. The P-DNA may be modified to facilitate cloning and should preferably not naturally encode proteins or parts of proteins. The P-DNA is characterized in that it contains, at each end, at least one border sequence, referred to as either a "P-DNA border sequence" or "P-DNA border-like sequence," which are interexchangeable terms. See the definition of a "border sequence" and "border-like" above. A P-DNA may also be regarded as a "T-DNA-like" sequence, see definition below.

Plant and plant parts: includes angiosperms and gymnosperms such as potato, tomato, tobacco, alfalfa, lettuce, carrot, strawberry, sugarbeet, cassava, sweet potato, soybean, maize, turf grass, wheat, rice, barley, sorghum, oat, oak, eucalyptus, walnut, and palm. Thus, a plant may be a monocot or a dicot. The word "plant," as used herein, also encompasses plant cells, seed, plant progeny, propagule whether generated sexually or asexually, and descendents of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent. A "selected plant species" may be, but is not limited to, a species of any one of these "plants."

Any of such plant parts can be transformed according to the present invention. Thus, the method of the present invention is suitable for callus transformation, immature embryo transformation, pollen transformation, shoot apex transformnation, e.g., transformation of an excised shoot apical tissue by inoculating the tissue with a transformation bacterium, in planta transformation, floral transformation, and seed transformation.

Progeny plant: a progeny plant is an offspring of a parent plant and in the case of the present invention may be a genetically identical offspring of a plant grown from a seedling that has been transformed according to the present invention.

Regulatory sequences: refers to those sequences which are standard and known to those in the art, that may be included in the expression vectors to increase and/or maximize transcription of a gene of interest or translation of the resulting RNA in a plant system. These include, but are not limited to, promoters, peptide export signal sequences, introns, polyadenylation, and transcription termination sites. Methods of modifying nucleic acid constructs to increase expression levels in plants are also generally known in the art (see, e.g. Rogers et al., 260 *J. Biol. Chem.* 3731-38, 1985; Cornejo et al., 23 *Plant Mol. Biol.* 567: 81,1993). In engineering a plant system to affect the rate of transcription of a protein, various factors known in the art, including regulatory sequences such as positively or negatively acting sequences, enhancers and silencers, as well as chromatin structure may have an impact. The present invention provides that at least one of these factors may be utilized in engineering plants to express a protein of interest. The regulatory sequences of the present invention are native genetic elements, i.e., are isolated from the selected plant species to be modified.

Terminator: A construct of the present invention can be used to efficiently reduce or prevent the transcription or translation of a target nucleic acid by triggering convergent transcription of a desired polynucleotide. One particular characteristic of such a construct is that no functional terminator is operably linked to the desired polynucleotide. Accordingly, the construct could be regarded as "terminator-free."

A terminator is a genetic element that (1) defines transcript size and (2) processes the transcript to increase its stability and transport competency. Such an element needs to contain the binding sites for proteins that are involved in 3'-end cleavage and polyadenylation.

In this regard, plant terminators may contain, among others, (1) a UUUUUA[A/U]UUU-like motif (SEQ ID NO: 7) that functions as cleavage and polyadenylation site, (2) an A-rich region of about six to 10 bases situated between about 13 and 30 bases upstream from the cleavage site, (3) sequences as far as 90 bases upstream from the cleavage site that either comprise UG or UUGUAA-like motifs, and (4) UUUUU or GUGUU-like sequences downstream from the cleavage site.

Obviously, a terminator needs to comprise all components that make it effective in both defining transcript size and transcript processing to avoid activation of transcript degradation mechanisms. One such mechanisms is activated when RNA surveillance detects pre-mRNAs that contain premature termination codons (Maniatis and Reed, Nature 416: 499-506, 2002). It should be understood that a terminator needs to display a reasonable efficacy in order to be designated as such. Thus, a terminator needs to be able to support production of transcripts that generally share a same or similar size. Sequences that display less than about 25% termination activity and would not be used for the effective expression of genes-of-interest in transgenic plants are not terminators.

Typically, there exist a few well-known terminators that are used in the field in designing gene silencing constructs. On of the more frequently used terminators, for instance, is the *Agrobacterium* nopaline synthase (nos) gene terminator, which comprises both 3' untranslated sequences and some additional downstream DNA. Other terminators include:

The 3' untranslated sequences of T-DNA gene 7 (Genbank accession V00090)

The 3' untranslated sequences of the major inclusion body protein gene of cauliflower mosaic virus The 3' untranslated sequences of the pea ribulose 1,5-bisphosphate carboxylase small subunit (Genbank accession M21375)

The 3' untranslated sequences of the potato ubiquitin-3 gene (Genbank accession Z11669).

The 3' untranslated sequences of the potato proteinase inhibitor II gene (Genbank accession CQ889094).

It may be desirable to construct a desired DNA region or transfer-DNA cassette that does not comprise any of such terminators. That is, the construct does not contain a functional terminator or a terminator that is preceded by a self-splicing ribozyme-encoding sequence that is operably linked to a desired polynucleotide.

Target species: species of the plant that is to be transformed.

Transformation of plant cells: a process by which DNA is stably integrated into the genome of a plant cell. "Stably" refers to the permanent, or non-transient retention and/or expression of a polynucleotide in and by a cell genome. Precise cutting-mediated transformation can result in the stable transformation of new shoots that arise from the cut surface of seedlings. These shoots can develop into the aboveground portions of a plant and consequently give rise to transformed progenies. Thus, a stably integrated polynucleotide is one that is a fixture within a transformed cell genome and may be replicated and propagated through successive progeny of the cell or resultant transformed plant. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, sand, electroporation, heat shock, lipofection, polyethylene glycol treatment, micro-injection, and particle bombardment.

Hence, a cut/cotyledonless/decapitated seedling of the present invention may be subjected to any of these alternative transformation methods, not necessarily an *Agrobacterium*-mediated transformation method. For instance, cut seedlings may be bombarded by microparticles coated in desired DNA molecules; or a cut seedling may be placed into appropriate DNA solution and electroporated.

Transformation may occur under natural or artificial conditions using various methods well known in the art. See, for instance, Methods in Plant Molecular Biology and Biotechnology, Bernard R. Glick and John E. Thompson (eds), CRC Press, Inc., London (1993); Chilton, Scientific American, 248)(6), pp. 36-45, 1983; Bevan, Nucl. Acids. Res., 12, pp. 8711-8721, 1984; and Van Montague et al., Proc R Soc Lond B Biol Sci., 210(1180), pp. 351-65, 1980. See also de la Riva et al., Electronic Journal of Biotechnology, Vol. 1, Issue 3, 1998, which reviews *Agrobacterium*-mediated transformation parameters.

Transformation may rely on any known method for the insertion of nucleic acid sequences into a prokaryotic or eukaryotic host cell, including the bacterium-mediated transformation protocols described herein, such as *Agrobacterium*-mediated transformation, or alternative protocols, such as by viral infection, whiskers, electroporation, heat shock, lipofection, polyethylene glycol treatment, micro-injection, and particle bombardment.

A "transformation vector" is a plasmid that can be maintained in a bacterium, such as *Agrobacterium*, and contains at least one right border or variant thereof as described herein. Infection of explants with such bacterium strains carrying a transformation vector and application of transformation procedures will produce transformed calli, shoots, and/or plants that contain at least part of the transformation vector stably integrated into the plant cell genome.

A transformation vector of the present invention may comprise a transfer-DNA that comprises some, all, or any combination of the nucleic acid elements described herein. For instance, all or some of the transfer-DNA components may be native or foreign with respect to the genome of the plant species being transformed.

The skilled person understands what is meant by "transfer-DNA" and how to manipulate it accordingly. A transfer-DNA ("T-DNA") is a genetic element that is well-known as an element capable of integrating a nucleotide sequence contained within its borders into another nucleotide. In this respect, a T-DNA is flanked, typically, by two "border" sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleic acids, like promoter and terminator regulatory elements that facilitate its expression, i.e., transcription and/or translation of the DNA sequence encoded by the desired polynucleotide or selectable marker.

The desired DNA region, for instance, may be created in another plasmid and then inserted into the transfer-DNA of a transformation vector. The desired DNA region may contain a polynucleotide of interest that is operably linked to a promoter to drive its expression but is not operably linked to a terminator element or to a sequence involved in polyadenylation.

The sequence of a transfer-DNA may be from a bacterium species like *Agrobacterium*, or it may be isolated from a plant species, such as a P-DNA described herein. Alternatively, a transfer-DNA may be constructed artificially by subcloning only T-DNA border sequences to one or both ends of a desired DNA region.

In this respect, and similar to the case with the transfer-DNA sequence, the border sequence may be from an *Agrobacterium* species or may be derived from a sequence native to the genome of the plant being transformed, which is capable of initiating docking and the "nicking" activity of various pertinent *Agrobacterium* enzymes, such as virD2.

Variant: a "variant," as used herein, is understood to mean a nucleotide or amino acid sequence that deviates from the standard, or given, nucleotide or amino acid sequence of a particular gene or protein. The terms, "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software.

Vortex: any vortexer equipment can be used to perform the vortexing step of the present invention. That is, once the seedling has been cut, for instance when an alfalfa germinating seedling has been cut at the position where the two cotyledons meet, and placed into a bacterium suspension, the suspension can be vortexed by placing it on a vortexing machine for a desired length of time.

In this respect, the Vortex-Genie (Scientific Industries) series of vortexers, such as Vortex-Genie 1, Vortex-Genie 2, and Vortex-Genie 2T can be employed. A suspension of bacterium and prepared seedling can be vortexed at any speed (revs per minute), such as at any of the following approximate speeds: 5, 10, 15, 20, 25, 30, 35, 40, 45, 50, 55, 60, 65, 70, 75, 80, 85, 90, 95 100, 110, 120, 130, 140, 150, 160, 170, 180, 190, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 4000, 5000, 6000, 7000, 8000, 9000, or 10000 rpm, or any integer in between. It is possible to modulate the speed at which a prepared plant sample is vortexed and the length of time vortexing at particular speeds takes place.

It also is possible to employ a vortexing step without actual knowledge of the precise speed, e.g., rpm, the vortex is shaking. For instance, it is possible to perform the present methodology by relying on the speed setting indicated on the vortexing machine. For example, one may vortex a plant-bacterium suspension for five minutes at setting "8" of Vortex-Genie 2.

One of skill in the art will find that it is empirical to determine what speed or what vortex speed setting is optimal, or not detrimental, to the integrity of the decapitated seedling being vortexed in terms of transformation efficiency.

Similarly, the skilled artisan can readily determine the length of time that is desirable to subject a cut seedling to vortexing. For instance, a vessel containing a bacterium suspension and immersed cut seedlings may be vortexed for 1, 2, 3, 4, 5, 6, 7, 8, 9, 10, 11, 12, 13, 14, 15, 16, 17, 18, 19, 20, 25, 30, 35, 40, 45, 50, 55, or 60 minutes, or more than 60 minutes, or any integer in between.

A goal of such vortexing is to ensure the transformation bacterium containing a transformation plasmid comes into contact with the plant cells of the decapitated seedling that have been exposed due to the excision made thereon. That is, it is desirable to ensure the bacterium enters into the cut surface of the seedling. In the case of a germinating alfalfa seedling, therefore, it is desirable for the bacterium suspension to be vortexed at an optimal level to ensure that bacteria enters at the cut surface. Furthermore, the bacterium suspension may comprise an abrasive substance, such as sand, whiskers, glass particles that facilitate the exposure of plant cells to bacteria comprising a transformation vector.

The temperature at which vortexing or equivalent agitation is performed can be at room temperature or in a cold room, if desired. The temperature may be optimized to suit or facilitate transformation efficiencies depending on the species of the plant being transformed.

It is desirable to optimize such parameters to minimize or abolish cell disintegration or cellular damage. Any seedling from any plant species, therefore, can be treated in such a vortexing fashion and any of such parameters, like the length of time of vortexing and the speed of vortexing, can be modulated and optimized for the particular seedling and species to enhance transformation efficiencies. Hence, the present method works independently of plant species; it is a species-independent transformation method.

Any person of skill in the art would know how to culture the incised or excised seedling of any species once the seedling has been inoculated with the bacterium suspension to produce a plant from the transformed seedling.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

One such method entails (a) exposing a seedling that has been cut in such a way that the seedling is able to produce a new shoot at the cut surface to at least one bacterium strain that contains a transformation plasmid carrying a desired polynucleotide; (b) growing a plant from the seedling; and (c) identifying whether the desired polynucleotide is integrated into the genome of the plant.

A seedling from any plant species can be so treated but legumes are one particular plant of interest. Thus, the present invention contemplates treating legume explants, such as seedlings from alfalfa, pea, soybean, peanut, chickpea, and barrel medic.

Bacteria species and strains other than those of *Agrobacterium*, e.g., *Agrobacterium tumefaciens*, can be used to transforrn one such plant. For instance, any genera within the family Rhizobiaceae can be used in place of *Agrobacterium* to transform a plant like alfalfa. For example, members of the *Rhizobium* and *Phyllobacterium* genera can be used. Examples of transforming bacteria other than those used in *Agrobacterium*-mediated transformation, include, but are not limited to, *Rhizobium trifolii, Rhizobium leguminosarum, Phyllobacterium myrsinacearum, Sinorhizobium meliloti, Mesorhizobium loti* bacterial strains, which can be used to transform a plant according to the present invention. See Broothaerts et al., Nature, 433, pp. 629-633, 2005, which is incorporated herein by reference.

Once the seedling, for example an alfalfa germinating seedling, has been cut as described above, it is then immersed in a suspension of any one of the bacteria described herein. Once the cut seedling is so immersed, the suspension may be vortexed.

On the other hand, the step of exposing the cut seedling to a transforming bacterium may also comprise injecting or otherwise applying the bacterium to the specific site of the incision. This step may be combined with the immersion step.

Since there exist public concerns about plants and crops that contain foreign genetic elements, the present transformation plasmid limits the extent to which foreign genetic elements are introduced into the selected plant genome. For example, a desired polynucleotide contained within the transfer-DNA of the plasmid would comprise genetic sequences that are native to the species of the seedling or native to a plant that is interfertile with the target species. That is, the desired polynucleotide may be operably linked to at least one of a promoter, enhancer, or terminator that is endogenous to the species of the plant to be transformed. For instance, if the seedling is a germinating seedling from alfalfa, then the desired polynucleotide may be operably linked to a least one of a promoter, enhancer, or terminator that naturally occurs in, e.g., is native to, the alfalfa genome.

Preferably, all of the genetic elements that are ultimately transferred from the transformation plasmid to the plant genome are native to the plant. In such a case, the promoter, enhancer, and terminator, as well as the desired polynucleotide, are all endogenous to the plant species that is to be transformed. In one embodiment, at least one, if not all, of the genetic elements that are transferred from the plasmid to the plant genome are isolated from the same plant, or from a plant from the same species as the target plant, or from a plant that belongs to a species that is sexually interfertile with the species of the target plant.

A native genetic element is a nucleic acid that naturally exists in, originates from, or belongs to the genome of a plant that is to be transformed. Thus, any nucleic acid, gene, polynucleotide, DNA, RNA, mRNA, or cDNA molecule that is isolated either from the genome of a plant or plant species that is to be transformed, or is isolated from a plant or species that is sexually compatible, or interfertile with the plant species that is to be transformed, is "native" to, i.e., indigenous to, the plant species. In other words, a native genetic element represents all genetic material that is accessible to plant breeders for the improvement of plants through classical plant breeding. For instance, native DNA incorporated into cultivated alfalfa can be derived from any genotype of alfalfa or any genotype of a wild alfalfa species that is sexually compatible with alfalfa.

Any variants of a native nucleic acid also are considered native in accordance with the present invention. In another embodiment, therefore, a native nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence.

A native nucleic acid isolated from a plant may also encode a variant of the naturally occurring plant protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in amino acid sequence to the unmodified, native protein expressed in the plant from which the nucleic acid was isolated.

Accordingly, in one embodiment, the present method entails limiting the number of non-native genetic elements into the transformed plant. Ideally, in one embodiment, the method does not introduce any foreign nucleic acids into the genome of the plant. In one embodiment, a foreign nucleic acid is one that is derived from non-plant organisms, or derived from a plant that is not the same species as the plant to be transformed or is not derived from a plant that is not interfertile with the plant to be transformed, does not belong to the species of the target plant. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product. According to the present invention, a most desired transgenic plant is one that contains minimal, if any, foreign nucleic acids integrated into its genome. The present invention also encompasses transgenic plants that do contain non-plant species nucleic acids in their genomes.

It is desirable to insert into the genome of a plant a desired DNA molecule or desired polynucleotide that alters one or more traits associated with the plant. For instance, expression of the desired polynucleotide in the stably transformed plant confers a trait to the plant selected from the group consisting of increased drought tolerance, reduced height, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved taste, improved texture, decreased phosphate content, increased germination, increased micronutrient uptake, improved starch composition, improved flower longevity, and production of novel proteins or peptides.

With respect to alfalfa, it is desirable to insert a polynucleotide into the alfalfa genome using the present inventive method to reduce expression of endogenous caffeic acid o-methyltransferase (Comt) or caffeoyl CoA 3-O-methyltransferase (Ccomt) genes. Reducing the expression of these particular genes decreases lignin content in alfalfa, thereby enhancing the nutritional value of alfalfa forage.

The desired polynucleotide in this case could be one that is designed in an antisense fashion to bind or anneal to a Comt or Ccomt RNA transcript. For instance, the desired polynucleotide may be all of part of the 5'-untranslated region of the Comt or Ccomt gene, all or part of the 3'-untranslated region of either gene, all or part of the leader sequence associated with either gene, or all or part of the trailer sequence associated with either gene.

Alternatively, an RNAi approach could be used to design the desired polynucleotide so that a hairpin or double-stranded RNA duplex is formed upon expression, which initiates downregulation of either or both of these particular genes.

It also is desirable to use the present inventive method to integrate into the alfalfa genome a desired polynucleotide that increases proanthocyanidin levels in the cell.

Other genes can be so targeted, not only those for Comt, Ccomt, and proanthocyanidin. For instance, a targeted gene may be one that encodes a protein that is selected from the group consisting of an antifungal, a nutritional peptide or protein, a transcription factor, a receptor that binds to pathogen-derived ligands, a hemoglobin, an oxidase, an enzyme of the lignin biosynthesis pathway, an enzyme of industrial value, or an antigen.

It is routine to determine whether a desired polynucleotide is integrated into the plant genome. For instance, one may identify an integration event qualitatively or genetically. That is, after employing the transformation method described herein, one could compare one or more traits between the plant obtained from the seedling or a progeny thereof and a wild-type plant of the same species, where a difference in a particular trait between the wild-type and obtained plants indicates that the desired polynucleotide is integrated into the plant genome.

Alternatively, the polymerase chain reaction may be employed to amplify nucleic acids extracted from the obtained plant or progeny thereof to determine whether all or part of the desired polynucleotide can be isolated therefrom.

Similarly, a nucleic probe may be employed in a Northern or Southern blot, for instance, to identify the presence of the desired polynucleotide in the plant genome or of its RNA transcript from a cell extract. It is also possible to test the plant cell extract for the presence or absence of a particular protein product, if any, of the desired polynucleotide, by applying methods such as ELISA.

A method for determining whether the desired polynucleotide is integrated into the plant genome also may entail assaying the cell for downstream effects of expression of the desired polynucleotide. For instance, one may determine whether the expression level of an endogenous gene is altered in comparison to the expression level of the same gene in a wild-type plant of the same species. The amount or presence or absence of the gene's RNA transcript or the gene's protein product is indicative of the gene's expression level.

The following examples serve to illustrate various embodiments of the present invention and should not be construed, in any way, to limit the scope of the invention.

All references cited herein, including patents, patent application and publications, are hereby incorporated by reference in their entireties, where previously specifically incorporated or not.

Having now fully described this invention, it will be appreciated by those skilled in the art that the same can be performed within a wide range of equivalent parameters, concentrations and conditions, without undue experimentation. This application is intended to cover any variations, uses, or adaptations of the invention, following in general the principles of the invention, that include such departures from the present disclosure as come within known or customary practice within the art to which the invention pertains and as may be applied to the essential features hereinbefore set forth.

EXAMPLES

Example 1

Vortex-Mediated Transformation of Alfalfa

This experiment evaluated the applicability of an alfalfa seedling as an explant source for *Agrobacterium*-mediated transformation. Mature seeds of alfalfa were:

(1) immersed in 70% ethanol for three to five minutes;
(2) vortexed in 25% (v/v) bleach (6.0% sodium hypochlorite) for 15 minutes; and
(3) rinsed twice with sterilized water.

The resultant, sterilized seeds were then (4) germinated in the dark at 24° C. on seed germination medium, which consisted of Murashige and Skoog (MS) medium (Murashige, et al., *Physiologia Plantarum*, 15: 473-497, 1962) and 1% sucrose (pH 5.7). Germination time was limited to the minimum time required for exposure of apical meristems. In case of alfalfa this time window was three days.

Young seedlings were then (5) emerged into a tube containing a suspension of *Agrobacterium* LBA4404 carrying the β-glucuronidase (gus) gene.

The *Agrobacterium* suspension was obtained by (i) inoculating 30 mL of LB liquid medium (Sigma, St. Louis) containing the appropriate antibiotics with *Agrobacterium*, and then incubating the inoculated suspensions overnight at 28° C. under constant rotation at 250 rpm; (ii) optionally adding 50 μM of acetosyringone (AS) four hours prior to infection; (iii) precipitating the cells by centrifugation for 15 minutes at 3600 rpm (Beckman GH-38 rotor); (iv) resuspending the cells in 15 mL of MS salts, B5 vitamins (Gamborg, et al., 1968) and 3% sucrose (pH 5.7) (vortexing infection medium, VIM) to an $OD_{600}$ of 0.6-0.7 in 50-mL centrifuge tube, and adding 0.03% Silwet77 (Lehle Seeds, Round Rock, Tex.), and (iv) adding 550 mg sterile sand.

The tube containing seedlings and *Agrobacterium* was placed in a large sample set platform head and vortexed (Vortex-Genie II mixer, Scientific Industries) for 30 minutes at the highest speed (setting at "8"; about 3,200 rpm) at room temperature to allow swirling of the sand in the suspension.

Seedlings were then transferred to co-cultivation medium (0.5 MS medium, 1.5% sucrose, 2.0 g $L^{-1}$ phytagel, pH 5.8). Petri plates were sealed with parafilm and incubated for 24 hours at 24° C. with a 16 hour photoperiod.

Following the co-cultivation period, all seedlings were transferred seedling development medium (SDM) consisting of half-strength MS medium, 1.5% sucrose, 300 mg $L^{-1}$ timentin and 2.0 mg $L^{-1}$ phytagel (pH 5.8). Plates were stored at 24° C. with a 16 hour photoperiod in a Percival culture chamber.

After two weeks on SDM, the established plantlets were then transferred to soil and acclimated to lower humidity at 24° C. with a 16 hour photoperiod in an environmental growth chamber. These primary putative transgenic plants were denoted as "T0 plants."

After three days in the environmental growth chamber, histochemical assays were performed to visualize DNA transfer by virtue of gus-staining patterns. These assays were performed according to Jefferson et al., EMBO J 6: 3901-3907, 1987. Basically, the GUS substrate buffer consisted of 5-bromo-4-chloro-3-indoyl-glucuronide (X-Gluc, 0.3% w/v), potassium ferricyanide (5 mM), potassium ferrocyanide (5 mM), sodium phosphate (0.1M; pH 7.0), and Triton X-100 (0.5% v/v). Staining was performed overnight at 37° C. and tissues were immersed in 70% ethanol to remove the chlorophyll.

The assays evidenced limited gus gene expression in six-day old seedlings as visualized by the presence of small blue foci on less than 30% of treated seedlings, indicating low DNA transfer frequencies.

Additional fluorometric assays were performed to quantify DNA transfer rates. Fluorometric analysis was conducted by applying a modified protocol according to Lin et al. Focus 16: 72-77, 1994. Alfalfa tissue was homogenized with GUS extraction buffer containing 50 mM $NaPO_4$ (pH 7.0), 10 mM dithiothreitol (DTT), 1 mM Na$_2$EDTA, 0.1% sodium lauryl sarcosine, 0.1% Trition X- 100 and centrifuged at 12,000×g for 30 min. One to three μl of clarified tissue extract was used to determine the protein content using the Bradford protein assay and a Beckman DU 530 spectrophotometer. Twenty μg of protein was added to 500 μl of 4-methyl-β-D-glucuronide (MUG) assay buffer (1 mM MUG in GUS extraction buffer), vortex and incubated at 37° C. overnight. After incubation, 25 μl of the reaction mixture was added to 225 μl of stop buffer (0.2 M Na$_2$CO$_3$). Four-methylumbellifore (MU) concentrations were determined using a Bio-Tek FLx800 fluorometer at 595 nm. The values obtained were converted to pmol MU per mg protein per hour.

In an effort to enhance DNA transfer frequencies, a 0.7-kilo basepair (kb) expression cassette for the *E. coli* replication-associated rom gene depicted in SEQ ID NO: 1 (Atlung et al., 1999) was inserted into the backbone of the transformation vector, pSIM387. This resulted in an almost 10-fold increased level of transient gus activity, as determined fluorometrically. Thus, plasmid copy number control appears to increase the frequency of DNA transfer to alfalfa cells.

An indication for a further increase of DNA transfer frequencies was obtained by replacing the original octopine-type LBA4404 with the nopaline strain C58C1 (Koncz and Schell, Mol Gen Genet 204: 383-396, 1986). Seedling infection with the new strain containing pSIM387 resulted in 2.6-fold higher gus activity levels than determined for the original strain carrying this vector.

To determine stable transformation frequencies, seedlings were infected with C58C1::pSIM387, recovered on plates, and transferred to soil. A total of 6.2% of three-week old seedlings contained leaves that displayed at least some gus activity. This frequency was increased by supplementing the *Agrobacterium* suspension with acetosyringone (7.5%).

Despite these relatively high transformation frequencies, none of the assayed plants contained leaves that fully stained for gus activity. Furthermore, upper leaves of these plants lacked any gus activity. These two observations suggested that the vortex-enhanced infection of intact alfalfa seedlings resulted in transformation of somatic rather than germline cells. Because somatic cell transformation would not be predicted to result in heritably stable events, the original transformation procedure was modified and encompassed the excision of cotyledon tissues, either at random positions or precisely where two cotyledons meet, which is at the thickest part of the stem segment (FIGS. 1A and B).

Upon infection, the cut seedlings quickly recovered and developed new shoots (FIG. 1B). Histochemical analysis demonstrated that random cutting only slightly increased the incidence of stable somatic cell transformation (8%). In contrast, precise cutting was found to triple the number of plants that contained leaves expressing the gus gene (17.3%). Importantly, 3% of plants derived from this latter treatment contained upper leaves that fully stained for gus activity. Application of the method to other larger-seeded crops was found to also provide marker-free vortex-mediated seedling (VMS) transformation of crops including *Brassica napus* (canola) (FIG. 1D) and *Beta vulgaris* (sugarbeet).

Individual alfalfa plants exhibiting the 'all-blue upper leaf' (ABUL) phenotype were transferred to soil and grown in the greenhouse to mature plants, which were hand pollinated and allowed to set seed. In all cases, progeny analyses demonstrated successful transgene transmission, with two T1 families segregating in Mendelian fashion and the other three displaying segregation ratios of 1:0, 1:7, and 1:2 respectively. See Table I. On average, 39% of T1 plants derived from ABUL T0 plants displayed a gus-positive phenotype, indicating an overall transformation frequency for VMS transformation of approximately 1%. These results demonstrate that seedlings can be used for the marker-free transformation of alfalfa. They also show that the upper leaves phenotype of three-week old infected plants is indicative for the plant's ability to transmit a transgene to the next generation.

TABLE I

Transgenic plants in selfed alfalfa progenies.

| Line | Total Progeny analyzed | Transgenic | Estimated segregation ratio |
|---|---|---|---|
| 185-3-10 | 24 | 24 (100%) | 1:0 |
| 185-3-16 | 24 | 3 (13%) | 1:7 |
| 185-3-26 | 24 | 15 (63%) | Mendelian |
| 185-3-29 | 24 | 20 (83%) | Mendelian |
| 185-3-31 | 24 | 9 (38%) | 1:2 |

The efficiency of identifying transformed seedlings can be enhanced by first categorizing seedlings into a group of relatively 'large' seedlings (75% of total) and a group of relatively 'small' seedlings (25% of total), and, second, only screening the group of small seedlings. Most transformed seedlings that will give rise to transformed progenies will be delayed in growth and development if compared to treated but untransformed seedlings.

In conclusion, it was found to be possible to transform alfalfa with native DNA only. One of these tools relates to an efficient marker-free transformation method, which is based on the vortex-mediated contacting of cut seedlings to *Agrobacterium* strains.

Excision of the tissues at the point where two cotyledons meet did not negatively affect further development of alfalfa seedlings. A second requirement for efficient transformation is that seedlings are vigorously vortexed while emerged in *Agrobacterium* suspensions. In contrast to ultrasound vibration, or sonication (Trick, Transgenic Research 6:329-336, 1997), this mechanical vibration did not trigger extensive cell wall disruption and/or cell death.

Several control experiments were carried out to demonstrate the efficacy of the transformation procedures. First, the significance of vortexing was demonstrated by comparing the alfalfa transformation frequencies for vortexed cut seedlings with that of similarly treated seedlings that were either submerged or gently agitated in an *Agrobacterium* solution with the seed coat removed only.

Hence, the following experiment was performed by removing the seed coats of three-day old alfalfa seedlings and immersing them into a 50 ml centrifuge tube containing 18 mL of an *Agrobacterium* strain carrying a binary vector with an intron-containing gus gene inserted between borders, 5.7 μL L-silwet, and 1 mL of sterile sand. Subsequently, the seedlings were (1) vortexed for thirty minutes at 3,200 rpm, (2) incubated for thirty minutes without agitation, and (3) gently agitated (Lab-Line Rotator, setting #6) for thirty minutes. After six days, cotyledons were removed from the seedlings and quantified using a fluorometric assay. Each treatment was repeated three times. The results are shown in Table II.

TABLE II

| | Average* | Standard Deviation | Standard Error |
|---|---|---|---|
| Vortex | 1.3449 | 1.4155 | 0.8172 |
| Gentle Agitation | 0.0281 | 0.0322 | 0.0186 |
| Submerge | 0.0117 | 0.0146 | 0.0084 |

*= units are in pmole/μg/hr

A second experiment was designed to demonstrate the importance of cutting the seedlings at precisely the indicated location. Precise cuts were made on three day old alfalfa seedlings. The treatments consisted of (a) Cut 1, which was made at the position where the two cotyledons meet; (b) Cut 2 was made 0.25 mm below Cut 1; (c) Cut 3 was made 0.50 mm below Cut 1, and (d) Cut 4 was made 0.75 mm below Cut 1. Seedlings were scored on the ability to develop growing shoots. Table III shows that only Cut 1 yields a high frequency of new shoots.

TABLE III

|       | % shoots* | % no shoots |
|-------|-----------|-------------|
| Cut 1 | 90        | 10          |
| Cut 2 | 20        | 80          |
| Cut 3 | 0         | 100         |
| Cut 4 | 0         | 100         |

*= units are in percent of seedlings having shoot development from total number seedlings.

Example 2

Regulatory Elements from Alfalfa

Apart from the availability of a marker-free transformation method, all-native DNA transformation requires native regulatory elements for the modified expression of the endogenous genes of interest. Anticipating the need for a specific promoter that drives gene expression mainly in the vascular system (see next section), a 0.9-kb alfalfa promoter homolog (SEQ ID NO: 2) of the bean phenylalanine ammonia-lyase (Pal2) gene, which is known to direct expression in the veins of tobacco plants (Liang et al., Proc Natl Acad Sci USA 86: 9284-9288, 1989), was isolated.

Sequence comparisons demonstrated that the alfalfa Pal2 promoter (Mspal2) region downstream from the predicted TATA box (promoter region I), mainly comprising the untranslated leader, is 62% homologous to that of the corresponding region of the bean Pal2 promoter. This homology declines to 49% for the upstream part of the promoter. Efficacy of the new alfalfa promoter was tested by linking it to an An2-like Myb transcription factor gene involved in accumulation of anthocyanins, designated Anh1. Transformation of tobacco with a binary vector containing this gene fusion resulted in the regeneration of transgenic plants that, if grown in the growth chamber, accumulated anthocyanins in the vascular tissues exclusively. This result indicates that the alfalfa Pal2 promoter has similar tissue specificity as reported for the Pal2 promoter from bean. Subsequent transfer of Pal2:Anh1 plants to the greenhouse resulted in a further upregulation of anthocyanin production, especially in the veins but also in other parts of leaves and stems, demonstrating that the Pal2 promoter is also inducible by high light.

In addition to the tissue-specific alfalfa Pal2 promoter, a candidate promoter for near constitutive above-ground gene expression was isolated. This promoter, shown in SEQ ID NO: 3, was isolated by applying inverse PCR methods and represents the 1.0-kb DNA sequence upstream from the alfalfa plastocyanin (PetE) gene.

Promoter activities were compared to that of the alfalfa small subunit ribulose-1,5-bisphosphate carboxylase/oxygenase (rbcS) gene, which drives above-ground gene expression levels at levels that are not sufficient for most commercial applications (Khoudi et al., Gene 197: 343-351, 1997). Transient assays demonstrated that the activity of the petE promoter surpassed that of the rbcS promoter. Subsequent analyses of progeny plants derived from transformed seedlings demonstrated that petE promoter activity maintained full activity.

To also obtain an alfalfa terminator sequence, a 0.4-kb sequence downstream from the RbcS gene depicted in SEQ ID NO: 4 was isolated.

This DNA fragment was used to replace the terminator of the *Agrobacterium* nopaline synthase (nos) gene linked to the gus gene. Histochemical assays of transiently transformed seedlings indicated that the 3'-rbcS sequence was at least as effective in supporting effective termination of gus gene expression as the conventional terminator. The results demonstrate that vortex-mediated seedling transformation can be used to rapidly assess the efficacy of new genetic elements in alfalfa. They also show utility of the alfalfa petE and Pal2 promoters, as well as rbcS terminator, as regulatory elements for high-level gene expression. By combining the various tools described herein it is possible to readily and reproducibly produce intragenic alfalfa plants.

Example 3

Vortex-Mediated Transformation of Canola

Procedures were basically the same as described for alfalfa. After two days of germination, seedlings were cut at the base of the cotyledons and infected by vortexing in a solution containing *Agrobacterium* carrying the gus reporter gene and sand. Seedlings were recovered by growing for seven days on G1 medium and subsequently transferred to soil. Table IV shows the frequency of four-week old seedlings displaying at least some gus gene expression.

TABLE IV

| Vortexing time | Transformation frequency | Standard Error |
|----------------|--------------------------|----------------|
| 15-minutes     | 35%                      | 4%             |
| 30-minutes     | 20%                      | 5%             |
| 45-minutes     | 9%                       | 5%             |

Example 4

Vortex-Mediated Transformation of Sugarbeet

Procedures were basically the same as described for alfalfa. However, the unique structure of the sugarbeet seed required the following modified method for explant preparation.

(1) Add sugarbeet seeds to a sterile 50 mL centrifuge tube up to the mL mark.

(2) In the laminar flow hood, add 25 mL 25% bleach solution and the content of a 1.5 mL tube autoclaved sand.

(3) Vortex on setting "7" for 30 minutes using the Vortex Genie with a large sample head for 50 mL tubes (Daigger).

(4) Wash with sterile water.

(5) Add 20 mL 3% $H_2O_2$, and vortex on setting "7" for 10 minutes.

(6) Remove $H_2O_2$ and do not rinse.

(7) Transfer seeds to water agar media, with cap side down.

(8) Wrap plates with parafilm, and incubate at 24° C. in a Percival growth chamber for four days.

(9) In the laminar flowhood, pry open the sugarbeet cap, and carefully transfer the germinating seedling to G1 medium place in the light at 24° C.

(10) After two days, seedlings were cut where the two cotyledons meet, and infected by vortexing in a solution containing *Agrobacterium* carrying the gus reporter gene and sand.

Analysis of four-week old plants derived from a vortex-mediated transformation demonstrated a transformation frequency of 6% with 1.5% displaying the desired "all-blue" phenotype.

Example 5

Vortex-Mediated Transformation of Lettuce

Employment of the alfalfa vortex-mediated transformation of cut seedlings was similarly effective in lettuce, with 89% of three-week old plants displaying stable transformation.

Example 6

Vector for All-Native Alfalfa DNA Transfer

SEQ ID NO:5 shows the sequence of a vector that can be used for the transformation of alfalfa with foreign, or preferably, all native DNA. The vector comprises the genetic elements needed for maintenance in both *E. coli* and *Agrobacterium*, and also contains alfalfa-derived upstream and downstream sequences that mediate DNA transfer and function as the ends of the actual transfer DNA. Any desired polynucleotide can be inserted between the upstream and downstream alfalfa sequences, for instance as a XbaI-ApaI fragment.

Example 7

Visual Markers

The transformation methods described in this invention were designed to efficiently produce transgenic or intragenic plants without introducing selectable marker genes into their genomes. Transformed plants can be identified by screening cut and infected seedlings for the presence of a transfer DNA that is free of a selectable marker gene. Such screening methods can be based on exploitation of the polymerase chain reaction. It is also possible to use transfer DNAs that contain a visual marker. One example of such a visual marker is the previously discussed beta-glucuronidase (gus) gene.

Alternatively, it is possible to use a gene encoding green fluorescent protein (gfp). One gfp gene is shown in SEQ ID NO.: 6. This gene can be fused to a strong promoter such as the alfalfa E9 promoter. A transformation vector containing an expression cassette for the gfp gene is pSIM1201. Seedlings can be screened for gfp gene expression by using, for instance, a fluorescent microscope or ELISA. In alfalfa, frequencies will range between about 0.5 and 5 percent.

Example 8

Cold Treatment

Alfalfa seeds were surface sterilized in 70% ethanol for 5 minutes, 20% bleach for 20 minutes and rinsed three times with sterile water. The treatments consisted of (a) sterile seeds placed on half strength MS medium and store in the dark at room temperature (~21° C.) for three days and (b) sterile seeds placed on half strength MS medium and store in the dark at room temperature (~21° C.) for three days followed by 24 hours in the dark at 4° C. Alfalfa seedlings were transformed via the vortex method with *Agrobacterium* containing a GUS vector. After six days the seedlings were histochemically assayed for entire cotyledon GUS staining compared to partial cotyledon GUS staining. Entire cotyledon GUS staining would be indicative of higher transformation efficiency. Each treatment was repeated three times.

|  | Average* | Standard Deviation | Standard Error |
|---|---|---|---|
| Room Temperature | 3.33 | 1.53 | 0.8819 |
| RT + 4° C. Or | 7 | 0 | 0 |

|  | % Entire | % Partial |
|---|---|---|
| Room Temperature | 14 | 86 |
| RT + 4° C. | 29 | 71 |

*= units are in number seedlings having entire GUS staining cotyledons.

What is claimed is:

1. A method for transforming a dicotyledonous plant, comprising (a) cutting a dicotyledonous plant seedling which has been allowed to germinate for about one to about eight days prior to cutting at the intersection of the stem where the cotyledons of the seedling meet to produce a decapitated seedling, (b) vortexing the decapitated seedling in a suspension of *Agrobacteria*, which comprises a transformation plasmid that carries a desired transfer DNA (c) cultivating at least one shoot from the decapitated seedling, (d) growing a plant from the shoot, and (e) identifying a plant that is stably transformed with the desired transfer DNA, wherein such a plant is a transformed dicotyledonous plant.

2. The method of claim 1, wherein the seedling is a seedling from alfalfa, pea, soybean, peanut, chickpea, canola, sugarbeet, clover, cotton, and barrel medic.

3. The method of claim 2, wherein the seedling is an alfalfa seedling.

4. The method of claim 3, wherein both cotyledons are excised from the seedling at the thickest part of the seedling stem where the cotyledons meet.

5. The method of claim 1, further comprising (a) growing the plant to produce seeds, (b) growing progeny plants from those seeds, and (c) identifying those progeny plants that are stably transformed with the desired transfer DNA, wherein such plants are transformed progeny plants.

6. The method of claim 1, wherein the seedling is germinated for one to eight days prior to cotyledon removal.

7. The method of claim 1, wherein the bacterium is *Agrobacterium tumefaciens*.

* * * * *